US010669673B2

(12) United States Patent
Chen et al.

(10) Patent No.: US 10,669,673 B2
(45) Date of Patent: Jun. 2, 2020

(54) MANUFACTURE OF ABSORBENT PAPER WITH LOW CHARGE DENSITY IMIDAZOLINIUM CONTAINING DEBONDER COMPOSITIONS

(71) Applicant: GPCP IP Holdings LLC, Atlanta, GA (US)

(72) Inventors: Yu Chen, Appleton, WI (US); Kevin M. Holtman, Appleton, WI (US); Brian S. Hammes, Appleton, WI (US); Jeffrey J. Boettcher, Neenah, WI (US)

(73) Assignee: GPCP IP Holdings LLC, Atlanta, GA (US)

( * ) Notice: Subject to any disclaimer, the term of this patent is extended or adjusted under 35 U.S.C. 154(b) by 166 days.

(21) Appl. No.: 15/868,073

(22) Filed: Jan. 11, 2018

(65) Prior Publication Data
US 2018/0202109 A1 Jul. 19, 2018

Related U.S. Application Data

(60) Provisional application No. 62/446,892, filed on Jan. 17, 2017.

(51) Int. Cl.
| | | |
|---|---|---|
| *D21H 21/24* | (2006.01) | |
| *D21H 21/20* | (2006.01) | |
| *D21H 17/07* | (2006.01) | |
| *C07D 233/16* | (2006.01) | |
| *D21H 17/20* | (2006.01) | |
| *D21H 27/00* | (2006.01) | |
| *D21H 17/14* | (2006.01) | |
| *D21H 17/37* | (2006.01) | |
| *D21H 21/18* | (2006.01) | |
| *D21H 21/22* | (2006.01) | |
| *D21H 17/06* | (2006.01) | |
| *D21H 17/00* | (2006.01) | |
| *D21H 23/06* | (2006.01) | |

(52) U.S. Cl.
CPC .......... *D21H 21/24* (2013.01); *C07D 233/16* (2013.01); *D21H 17/06* (2013.01); *D21H 17/07* (2013.01); *D21H 17/14* (2013.01); *D21H 17/20* (2013.01); *D21H 17/375* (2013.01); *D21H 17/72* (2013.01); *D21H 21/18* (2013.01); *D21H 21/20* (2013.01); *D21H 21/22* (2013.01); *D21H 23/06* (2013.01); *D21H 27/002* (2013.01)

(58) Field of Classification Search
CPC ........ D21H 17/06; D21H 17/07; D21H 17/14; D21H 17/20; D21H 17/375; D21H 17/72; D21H 21/18; D21H 21/20; D21H 21/22; D21H 21/24; D21H 23/06; D21H 27/002; C07D 233/16; A61K 31/787; C11D 1/94; C11D 3/001; C11D 1/62; C11D 1/835; A01N 2300/00

See application file for complete search history.

(56) References Cited

U.S. PATENT DOCUMENTS

| | | | |
|---|---|---|---|
| RE23,227 E * | 5/1950 | Blair et al. ............ | C23F 11/149 507/243 |
| 2,713,582 A * | 7/1955 | Smith ................... | C07D 233/04 548/313.7 |
| 3,556,932 A | 1/1971 | Coscia et al. | |
| 3,556,933 A | 1/1971 | Williams et al. | |
| 3,686,025 A | 8/1972 | Morton | |
| 3,700,623 A | 10/1972 | Keim | |
| 3,749,691 A * | 7/1973 | Kandathil ............... | C11D 1/94 510/516 |
| 3,755,220 A | 8/1973 | Freimark et al. | |
| 3,772,076 A | 11/1973 | Keim | |
| 3,849,435 A * | 11/1974 | Diery et al. ......... | C07D 233/14 548/350.1 |
| 3,994,771 A | 11/1976 | Morgan, Jr. et al. | |
| 4,102,737 A | 7/1978 | Morton | |
| 4,181,634 A | 1/1980 | Kennedy et al. | |
| 4,254,255 A | 3/1981 | Löbach et al. | |
| 4,265,810 A | 5/1981 | Bauman et al. | |
| 4,351,699 A | 9/1982 | Osborn, III | |
| 4,362,737 A | 12/1982 | Schafer et al. | |
| 4,374,737 A * | 2/1983 | Larson ................... | C09K 8/035 507/130 |

(Continued)

FOREIGN PATENT DOCUMENTS

| | | | |
|---|---|---|---|
| JP | 01144496 A | * | 6/1989 |
| JP | 07252800 A | * | 10/1995 |

(Continued)

OTHER PUBLICATIONS

Tsumadori, M in "Recent Trends of Surfactants in Fabric & Home Care Field" CD Proceedings 6th World Surfactant Congress CESIO, Berlin Germany, paper # 196, Jun. 21-23, pp. 1-6. (Year: 2004).*
D. Bajpai, et al., Fatty Imidazolines: Chemistry, Synthesis, Properties and Their Industrial Applications, Journal of Oleo Science, 2006, pp. 319-329, vol. 55, No. 7.
C.M. Latham et al., Short Synthesis of Chiral 4-Substituted (S)-Imidazolinium Salts Bearing Sulfonates and Their Use in γ-Selective Reactions of Allylic Halides with Grignard Reagents, European Journal of Organic Chemistry, Feb. 2012, pp. 699-707, vol. 2012, Issue 4, WILEY-VCH Verlag GmbH & Co. KGaA, Weinheim.
ESPY, Chapter 2: Alkaline-Curing Polymeric Amine-Epichlorohydrin Resins, Wet Strength Resins and Their Application (L. Chan, Ed.), 1994, pp. 13-44.
Westfelt, Chemistry of Paper Wet-Strength, I. A Survey of Mechanisms of Wet Strength Development, Cellulose Chemistry and Technology, 1979, pp. 813-825, vol. 13.

(Continued)

*Primary Examiner* — Jose A Fortuna
(74) *Attorney, Agent, or Firm* — Laura L. Bozek

(57) ABSTRACT

Absorbent sheet is manufactured utilizing a low charge density debonder composition comprising an imidazolinium surfactant-containing constituent selected from the group consisting of: (i) cationic imidazolinium surfactants with alkylalkenylhydroxy substitution; (ii) zwitterionic imidazolinium surfactants; and (iii) an ion paired surfactant mixture including a zwitterionic imidazolinium surfactant and a cationic surfactant and, in admixture with the imidazolinium surfactant-containing constituent, (iv) a nonionic surfactant.

18 Claims, 9 Drawing Sheets

(56) References Cited

U.S. PATENT DOCUMENTS

| | | | |
|---|---|---|---|
| 4,441,962 A | 4/1984 | Osborn, III | |
| 4,447,294 A | 5/1984 | Osborn, III | |
| 4,529,480 A | 7/1985 | Trokhan | |
| 4,529,803 A | 7/1985 | Tomalia et al. | |
| 4,544,756 A | 10/1985 | Patel | |
| 4,603,176 A | 7/1986 | Bjorkquist et al. | |
| 4,675,394 A | 6/1987 | Solarek et al. | |
| 4,786,421 A * | 11/1988 | Butterworth | C11D 3/3932 510/516 |
| 4,804,769 A | 2/1989 | Solarek et al. | |
| 4,866,151 A | 9/1989 | Tsai et al. | |
| 4,892,555 A * | 1/1990 | Leigh | C11D 3/0018/101 |
| 4,959,125 A | 9/1990 | Spendel | |
| 4,981,557 A | 1/1991 | Bjorkquist | |
| 4,983,748 A | 1/1991 | Tsai et al. | |
| 5,008,344 A | 4/1991 | Bjorkquist | |
| 5,049,315 A * | 9/1991 | Hitz | A61K 8/4946 424/70.19 |
| 5,085,736 A | 2/1992 | Bjorkquist | |
| 5,138,002 A | 8/1992 | Bjorkquist | |
| 5,151,522 A * | 9/1992 | Hitz | A61K 8/4946 548/112 |
| 5,217,576 A | 6/1993 | Van Phan | |
| 5,240,562 A | 8/1993 | Phan et al. | |
| 5,279,767 A | 1/1994 | Phan et al. | |
| 5,420,315 A | 5/1995 | Uhrig et al. | |
| 5,536,504 A | 7/1996 | Eugster et al. | |
| 5,593,691 A | 1/1997 | Eugster et al. | |
| 5,622,597 A | 4/1997 | Callen et al. | |
| 5,643,498 A * | 7/1997 | Li | B01F 17/0042 252/8.91 |
| 5,698,076 A | 12/1997 | Phan et al. | |
| 5,730,839 A | 3/1998 | Wendt et al. | |
| 5,753,079 A | 5/1998 | Jenny et al. | |
| 6,176,972 B1 | 1/2001 | Driaran et al. | |
| 6,180,661 B1 | 1/2001 | Eugster et al. | |
| 6,211,139 B1 | 4/2001 | Keys et al. | |
| 6,245,197 B1 | 6/2001 | Oriaran et al. | |
| 6,346,169 B1 | 2/2002 | Ikeda et al. | |
| 6,458,343 B1 | 10/2002 | Zeman et al. | |
| 6,623,746 B1 | 9/2003 | Wadle et al. | |
| 6,649,024 B2 | 11/2003 | Oriarian et al. | |
| 6,680,286 B1 * | 1/2004 | Kawaguchi | C11D 1/72 510/276 |
| 6,969,443 B1 | 11/2005 | Kokko | |
| 7,183,250 B2 * | 2/2007 | Rodrigues | C11D 1/83 510/351 |
| 7,585,388 B2 | 9/2009 | Yeh et al. | |
| 7,585,389 B2 | 9/2009 | Yeh et al. | |
| 7,585,494 B2 | 9/2009 | Lange et al. | |
| 7,662,257 B2 | 2/2010 | Edwards et al. | |
| 7,682,488 B2 | 3/2010 | Yeh et al. | |
| 7,736,464 B2 | 6/2010 | Kokko | |
| 7,850,823 B2 | 12/2010 | Chou et al. | |
| 7,951,266 B2 | 5/2011 | Kokko et al. | |
| 8,778,138 B2 | 7/2014 | Super et al. | |
| 8,852,399 B2 | 10/2014 | Neal et al. | |
| 9,506,201 B2 | 11/2016 | Furman et al. | |
| 10,016,354 B2 * | 7/2018 | Konradi | A61K 31/787 |
| 2003/0056917 A1 | 3/2003 | Jimenez | |
| 2004/0163182 A1 | 8/2004 | Nguyen | |
| 2004/0259758 A1 * | 12/2004 | Rodrigues | C11D 1/83 510/475 |
| 2005/0119146 A1 * | 6/2005 | Rodrigues | C11D 1/008 510/224 |
| 2007/0107863 A1 | 5/2007 | Edwards et al. | |
| 2007/0224419 A1 | 9/2007 | Sumnicht et al. | |
| 2012/0244095 A1 * | 9/2012 | Konradi | A61Q 17/00 424/61 |
| 2018/0202108 A1 * | 7/2018 | Chen | D21H 17/06 |
| 2018/0202109 A1 * | 7/2018 | Chen | D21H 17/06 |
| 2018/0296459 A1 * | 10/2018 | Konradi | A61Q 17/00 |

FOREIGN PATENT DOCUMENTS

| | | | | |
|---|---|---|---|---|
| JP | 2003171871 A * | 6/2003 | | |
| WO | WO-9849898 A1 * | 11/1998 | | A01N 43/50 |
| WO | WO-2017151084 A1 * | 9/2017 | | D21H 17/15 |
| WO | WO-2018136318 A1 * | 7/2018 | | C07D 233/16 |

OTHER PUBLICATIONS

Strazdins, Chapter 4: Application of Electrokinetics in Optimization of Wet-End Chemistry, Wet-Strength Resins and Their Application (L. Chan, Ed.), pp. 63-83, 1994.

International Search Report and Written Opinion in PCT/US2018/013046 dated May 8, 2018.

International Search Report and Written Opinion in corresponding PCT/US2018/013457 dated May 8, 2018.

Sheshenev, et al., New Chiral Zwitterionic Phosphorus Heterocycles: Synthesis, Structure, Properties and Application as Chiral Solvating Agents, Chemistry, A European Journal, 2013, pp. 8136-8143, vol. 19, Issue 25, Wiley-VCH Verlag GmbH & Co. KGaA, Weinheim.

PUBCHEM-CID 74935089 Create Date: Jul. 1, 2014, pp. 1-11.

International Preliminary Report on Patentability in corresponding PCT/US2018/013457 dated Oct. 4, 2018.

International Preliminary Report on Patentability in related PCT/US2018/013046 dated Oct. 22, 2018.

\* cited by examiner

TENSILE REDUCTION VS. DEBONDER DOSAGE

WET/DRY TENSILE (%)

TENSILE REDUCTION VS. DEBONDER DOSAGE

WET/DRY TENSILE (%)

DRY TENSILE VS. DEBONDER DOSAGE

TENSILE REDUCTION VS. DEBONDER DOSAGE

MANUFACTURE OF ABSORBENT PAPER WITH LOW CHARGE DENSITY IMIDAZOLINIUM CONTAINING DEBONDER COMPOSITIONS

CLAIM FOR PRIORITY

This application is based, in part, on U.S. Provisional Application No. 62/446,892, filed Jan. 17, 2017, entitled Zwitterionic Imidazolinium Surfactant and Use in the Manufacture of Absorbent Paper, the priority of which is hereby claimed and the disclosure of which is incorporated herein by reference.

TECHNICAL FIELD

The present invention relates to the use of certain debonder compositions in manufacture of absorbent sheet such as paper tissue or paper towel. The debonder compositions contain a ricinoleate-type imidazolinium surfactant or a zwitterionic imidazolinium surfactant, optionally in combination with a quaternary ammonium or cationic imidazolinium surfactant. The imidazolinium materials of the invention exhibit reduced charge density compared to conventional imidazolinium containing debonder compositions.

BACKGROUND

Imidazolinium cationic surfactants may be prepared by reaction of the corresponding imidazoline compound with dimethyl sulfate. See Bajpai, D., Fatty Imidazolines: Chemistry, Synthesis, Properties and Their Industrial Applications, J. Oleo Sci., Vol. 55, No. 7, 319-329 (2006), pp. 321-322. A hydroxy substituted fatty acid imidazoline is disclosed as CAS registry compound no. 93858-34-5, having a molecular formula C40 H75 N3 O3. Imidazolines are used in pharmaceutical compositions and as corrosion inhibitors.

Debonder compositions are used in connection with the manufacture of absorbent paper products such as paper tissue and paper towel to adjust tensile strength and provide softness. Among the most effective compounds are quaternary ammonium surfactants which are sometimes used together with nonionic surfactants. Debonders are used with numerous additives such as wet strength agents and so forth. See U.S. Pat. No. 3,755,220 to Freimark et al. (1973), Col. 2, lines 1-10. U.S. Pat. No. 6,969,443 to Kokko discloses debonder compositions, including imidazolium salts in combination with nonionic surfactants. This reference also discloses the use of additives, including charge modifiers, wet strength resins, retention aids and auxiliaries such as carboxymethylcellulose. See Cols. 10-12. So also, U.S. Pat. No. 6,649,024 to Oriarian et al. discloses absorbent products incorporating a variety of cationic debonders, including di- or trialkyl ammonium salts. United States Patent Application Publication No. US2004/0163182 to Nguyen discloses nonionic surfactants used in combination with amide substituted imidazolinium salts. See paragraph [0013]. U.S. Pat. No. 4,959,125 to Spendel (1990) discloses manufacture of absorbent sheet with ampholytic or zwitterionic surfactants. See Col. 11, lines 21-46. Note, also, U.S. Pat. No. 6,245,197 to Oriaran et al. which discloses mixtures of cationic quaternary ammonium surfactants and anionic surfactants.

Ricinoleic acid is disclosed for the manufacture of surfactants in numerous references. See U.S. Pat. No. 4,254,255 to Löbach et al., Col. 2, lines 33-57. Ricinoleic acid is disclosed for the manufacture of quaternary surfactants as is seen in U.S. Pat. No. 5,420,315 to Uhrig et al., throughout. See claim 1. U.S. Pat. No. 6,623,746 to Wadle et al. discloses polyol esters of ricinoleic acid at Col. 5, lines 52 and the '746 patent likewise discloses a variety of zwitterionic surfactants including imidazolines at Col. 6, lines 31 and following. U.S. Pat. No. 7,585,494 to Lange et al. discloses ester-containing cationic surfactants including surfactants containing ricinoleic acid. See Cols. 39-40, note especially Col 40, lines 1-5 which mentions imidazoliniums.

A significant drawback of conventional systems using quaternary ammonium salts is that these compounds contribute significantly to titratable charge and change zeta potential. Controlling charge and zeta potential of the furnish in the headbox is critical to papermachine performance especially retention of papermaking solids in the final product. The problem with adding too much cationic additive is that it will exceed the adsorption capacity of the fiber surfaces, based on either the surface area or the limited extent of negative charge of the surfaces of fibers and other solid surfaces in the furnish. Excess cationic additives beyond what adheres to the fibers is likely to cause foam, high biological oxygen demand (BOD) levels in the effluent, and poor retention and drainage. Conventional charge control agents such as carboxymethyl cellulose can adversely impact softness of the product. The use of charge control agents may be reduced or even avoided entirely when using the process and compositions of the present invention.

SUMMARY OF INVENTION

There is thus provided in one aspect of the invention a method of making absorbent sheet comprising: (a) preparing an aqueous furnish of papermaking fibers; (b) incorporating a debonder composition into the aqueous furnish, said debonder composition comprising an imidazolinium surfactant-containing constituent selected from the group consisting of: (i) cationic imidazolinium surfactants with alkylalkenylhydroxy substitution; (ii) zwitterionic imidazolinium surfactants; and (iii) an ion paired surfactant mixture including a zwitterionic imidazolinium surfactant and a cationic surfactant and, in admixture with the imidazolinium surfactant-containing constituent, (iv) a nonionic surfactant; (c) incorporating a cationic wet strength resin into the aqueous furnish; and (d) forming the papermaking furnish into absorbent sheet.

The debonder compositions of the invention are surprisingly effective as debonders especially when used in connection with cationic permanent or cationic temporary wet strength resins as hereinafter demonstrated.

The compositions and process of the invention also provide unexpected effectiveness in controlling charge in the furnish over a wide range of addition, as is seen in connection with charge density, titratable charge and zeta potential. The invention thus provides for high levels of debonder addition without consuming anionic charge of papermaking fibers, enabling higher levels of addition of other cationic additives such as retention aids and the like without compromising softness of the product by requiring cellulosic charge control agents.

One preferred family of imidazolinium surfactants is ricinoleate-type imidazolinium compounds of the formula:

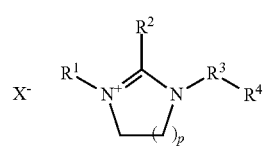

wherein:
R¹ is H, methyl, ethyl, or propyl;
R² is a hydroxy substituted alkylalkenyl moiety having from 11 to 21 carbon atoms;
R³ is an ethylene or propylene bridging group;
R⁴ is an amidoalkenylalkyl moiety bearing a pendant hydroxyl group having from 12 to 22 carbon atoms;
p is 1 or 2; and
X is selected from halides, sulfates, carboxylates and phosphates. Particularly preferred anions include Cl⁻, Br⁻, $CH_3OSO_3^-$, $C_2H_5OSO_3^-$, $NO_3^-$, $HCOO^-$ and $CH_3COO^-$.

Another preferred family of imidazolinium containing surfactants are ion paired surfactant mixtures comprising a zwitterionic imidazolinium surfactant and a cationic surfactant selected from cationic imidazolinium surfactants and quaternary ammonium surfactants, said zwitterionic imidazolinium surfactant having the structural formula I:

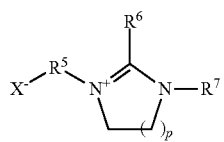

(I)

wherein:
R⁵ is a straight or branched hydrocarbon spacer moiety having from 2-18 carbon atoms wherein said R⁵ may be unsubstituted or optionally substituted with one or more groups which can be the same or different and are independently selected from the group consisting of halogen, cyano, alkyl, cycloalkyl, —OH, $O(C_1-C_6)$ alkyl, —C(=O)($C_1-C_6$) alkyl, —$CO_2H$, —C(=O)O($C_1-C_6$) alkyl, N[($C_1-C_6$) alkyl]₂, and —NH[($C_1-C_6$) alkyl] and/or may have interposed within said hydrocarbon spacer moiety one or more groups which may be the same or different and are independently selected from the group consisting of —NH—C(O)—, —C(O)—NH—, —O—, —$SO_2$— and —C(=O)—;
R⁶ is a straight or branched saturated or unsaturated hydrocarbon moiety having from 3 to 30 carbon atoms wherein said R⁶:
(i) may be unsubstituted or optionally substituted with one or more groups which can be the same or different and are independently selected from the group consisting of halogen, cyano, alkyl, cycloalkyl, —OH, $O(C_1-C_6)$ alkyl, —$CO_2H$, —C(=O)($C_1-C_6$) alkyl, —C(=O)O ($C_1-C_6$) alkyl, —N[($C_1-C_6$) alkyl]₂, —NH—C(O)($C_1$-$C_6$) alkyl, —C(O)$NH_2$, —C(O)—NH($C_1-C_6$) alkyl, and —NH($C_1-C_6$) alkyl, and/or
(ii) may have interposed within said hydrocarbon moiety one or more groups which may be the same or different and are independently selected from the group consisting of —NH—C(O)—, —C(O)—NH—, —O—, —$SO_2$— and —C(=O)—;
R⁷ is a straight or branched saturated or unsaturated hydrocarbon moiety having from 3 to 30 carbon atoms wherein said R⁷:
(i) may be unsubstituted or optionally substituted with one or more groups which can be the same or different and are independently selected from the group consisting of halogen, cyano, alkyl, cycloalkyl, —OH, $O(C_1-C_6)$ alkyl, —$CO_2H$, —C(=O)($C_1-C_6$) alkyl, —C(=O)O ($C_1-C_6$) alkyl, —N[($C_1-C_6$) alkyl]₂, —NH—C(O)($C_1$-$C_6$) alkyl, —C(O)$NH_2$, —C(O)—NH($C_1-C_6$) alkyl, and —NH($C_1-C_6$) alkyl, and/or (ii) may have interposed within said hydrocarbon moiety one or more groups which may be the same or different and are independently selected from the group consisting of —NH—C(O)—, —C(O)—NH—, —O—, —$SO_2$— and —C(=O)—;
wherein at least one of R⁶ or R⁷ or has from 8 to 30 carbon atoms;
X is selected from the group consisting of $SO_3$, $CO_2$, $PO_3$ and $HPO_2$; and
p is 1 or 2.

Further features and advantages will become apparent from the discussion which follows.

BRIEF DESCRIPTION OF DRAWINGS

The invention is described in detail below with reference to the drawings wherein.

DETAILED DESCRIPTION

Figure 1:
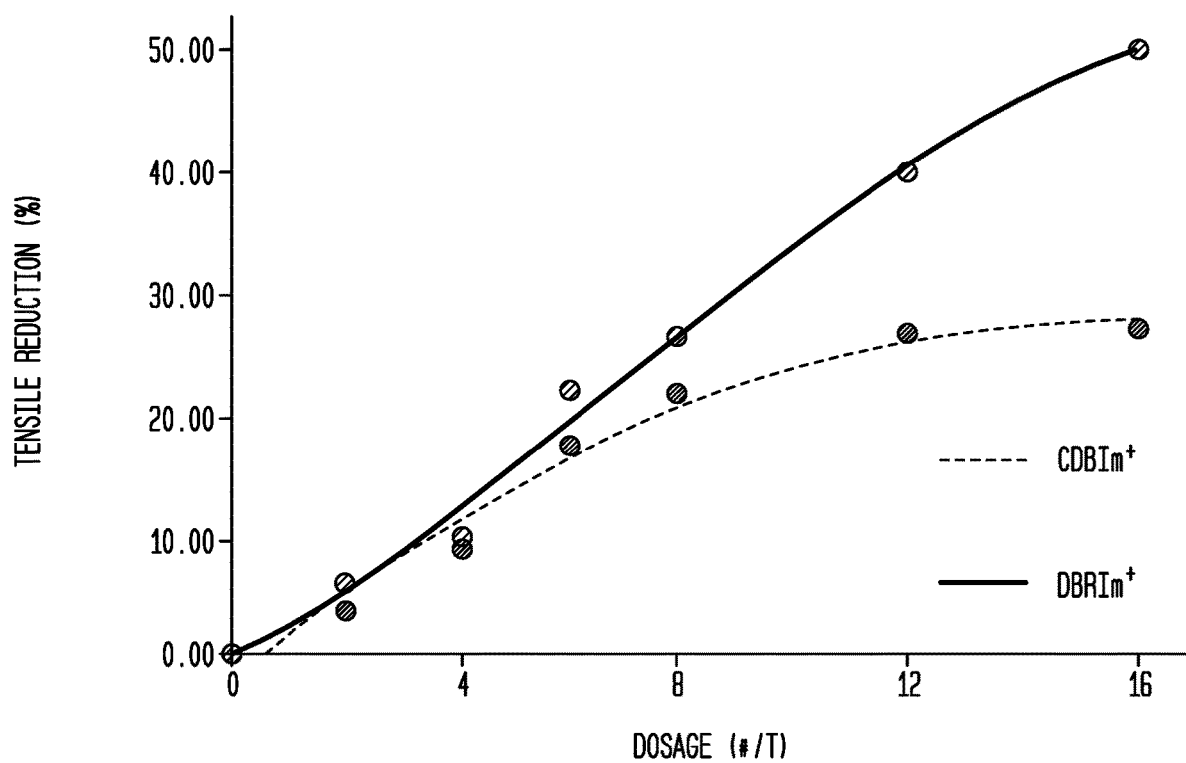
FIG. 1 is a plot of tensile reduction versus debonder dosage levels for towel-type handsheets incorporating debonder compositions with a ricineoleate-type surfactant and a control surfactant (labelled DBRIm⁺ and CDBIm⁺, respectively)

The invention is described in detail below in connection with the Figures for purposes of illustration only. The invention is defined in the appended claims. Terminology used herein is given its ordinary meaning consistent with the exemplary definitions set forth immediately below; g refers to grams, $m^2$ refers to square meters, percents, ppm and like terminology relates to weight percent, parts per million by weight and so forth unless otherwise indicated.

Add-on or dosage of various components in lbs/ton is expressed in lbs additive per ton of air dry pulp or papermaking fibers.

"Alkyl" means an aliphatic hydrocarbon group which may be straight or branched and comprising about 1 to about 30 carbon atoms in the chain. Branched means that one or more groups are attached to a linear alkyl chain. Alkyl may be unsubstituted or optionally substituted by one or more substituents which may be the same or different, each substituent being independently selected as provided herein.

"Alkenyl" means an aliphatic hydrocarbon group containing at least one carbon-carbon double bond and which may be straight or branched and comprising about 2 to about 30 carbon atoms in the chain. Branched means that one or more groups are attached to a linear alkenyl chain. Alkenyl may be unsubstituted or optionally substituted by one or more substituents which may be the same or different, each substituent being independently selected as provided herein.

"Cycloalkyl" means a non-aromatic mono- or multicyclic ring system comprising about 3 to about 10 carbon atoms, preferably about 5 to about 10 carbon atoms. The cycloalkyl can be optionally substituted with one or more substituents which may be the same or different, each substituent being independently selected as provided herein.

A hydroxy substituted alkylalkenyl moiety and like terminology refers to a group with alkyl, alkenyl portions and a hydroxy substitution, while an amidoalkenylalkyl moiety bearing a pendant hydroxyl group and like terminology refers to a group having alkyl and alkenyl portions, a hydroxy substitution as well as an amide functionality; typically connected to the surfactant molecule nucleus by way of the amido nitrogen of the amide functionality.

A hydroxy substituted alkylalkenyl moiety or amidoalkenylalkyl moiety bearing a pendant hydroxyl group referred to above or a hydrocarbyl group as illustrated and claimed herein may be without further substitution or optionally substituted with one or more additional groups which can be the same or different and are independently selected from the group consisting of halogen, cyano, alkyl, cycloalkyl, —OH, O($C_1$-$C_6$) alkyl, —$CO_2H$, —C(=O)($C_1$-$C_6$) alkyl, —C(=O)O($C_1$-$C_6$) alkyl, —N[($C_1$-$C_6$) alkyl]$_2$, —NH—C(O)($C_1$-$C_6$) alkyl, —C(O)$NH_2$, —C(O)—NH($C_1$-$C_6$) alkyl, and —NH($C_1$-$C_6$) alkyl, and/or may have interposed within said hydrocarbon moiety one or more groups which may be the same or different and are independently selected from the group consisting of —NH—C(O)—, —C(O)—NH—, —O—, —$SO_2$— and —C(=O)—. When we refer to a hydrocarbyl group or hydrocarbon moiety having interposed within it one or more groups such as —NH—C(O)—, —C(O)—NH—, —O—, —$SO_2$—, —C(=O)— and the like we refer to ether, amide, sulfone, ketone moieties and the like forming part of the chain such as ethylene oxide within the hydrocarbon chain.

"Consisting essentially of" and like terminology refers to the recited components and excludes other ingredients which would substantially change the basic and novel characteristics of the composition or article. Unless otherwise indicated or readily apparent, a composition or article consists essentially of the recited or listed components when the composition or article includes 90% or more by weight of the recited or listed components. That is, the terminology excludes more than 10% unrecited components.

"Ion paired surfactant mixtures" and like terminology as used herein refers to a surfactant mixture including a zwitterionic imidazolinium compound bearing an anionic moiety mixed with a cationic surfactant. The cationic surfactant may also be an imidazolinium surfactant or a quaternary ammonium surfactant as are known in the art. When mixed with nonionic surfactants to prepare a debonder composition, the debonder composition preferably exhibits a charge density of less than 0.3 meq/g.

Cationic Wet Strength Resins

Permanent and temporary cationic wet strength resins are often incorporated into tissue and towel absorbent paper products. Of particular utility for permanent wet strength resins are the polyamidoamine-epichlorohydrin wet strength resins, an example of which is sold under the trade name Amres® from Georgia-Pacific Resins, Inc. and Kymene 557LX and Kymene 557H by Hercules Incorporated of Wilmington, Del. These resins and the process for making the resins are described in U.S. Pat. Nos. 3,700,623 and 3,772,076. An extensive description of polymeric-epihalohydrin resins is given in Chapter 2: *Alkaline-Curing Polymeric Amine-Epichlorohydrin* by Espy in *Wet Strength Resins and Their Application*, pp. 13-44 (L. Chan, Editor, 1994). A reasonably comprehensive list of wet strength resins is described by Westfelt in *Cellulose Chemistry and Technology* Volume 13, pp. 813-825, 1979.

Temporary cationic wet strength resin may be any one of a variety of water-soluble organic polymers comprising aldehydic units and cationic units used to increase dry and wet tensile strength of a paper product. Such resins are described in U.S. Pat. Nos. 4,675,394; 5,240,562; 5,138,002; 5,085,736; 4,981,557; 5,008,344; 4,603,176; 4,983,748; 4,866,151; 4,804,769 and 5,217,576. Modified starches sold under the trademarks CO-BOND® 1000 and CO-BOND® 1000 Plus, by National Starch and Chemical Company of Bridgewater, N.J. may be used. Prior to use, the cationic aldehydic water soluble polymer can be prepared by preheating an aqueous slurry of approximately 5% solids maintained at a temperature of approximately 240° F. and a pH of about 2.7 for approximately 3.5 minutes. Finally, the slurry can be quenched and diluted by adding water to produce a mixture of approximately 1.0% solids at less than about 130° F.

Temporary wet strength agents of glyoxylated polyacrylamide resins are commonly produced by reacting acrylamide with diallyl dimethyl ammonium chloride (DADMAC) to produce a cationic polyacrylamide copolymer which is ultimately reacted with glyoxal to produce a cationic cross-linking temporary or semi-permanent wet strength resin, glyoxylated polyacrylamide. These materials are generally described in U.S. Pat. No. 3,556,932 to Coscia et al. and U.S. Pat. No. 3,556,933 to Williams et al. Resins of this type are commercially available under the trade name of Kemira Fennorez® 110 or PAREZ 631NC (Cytec). Different mole ratios of acrylamide/DADMAC/glyoxal can be used to produce cross-linking resins, which are useful as wet strength agents. Furthermore, other dialdehydes can be substituted for glyoxal to produce wet strength characteristics.

Cellulosic Sheet, Components and Related Terminology

The term "cellulosic", "cellulosic sheet" and the like are meant to include any product incorporating papermaking fiber having cellulose as a major constituent. "Papermaking fibers" include virgin pulps or recycle (secondary) cellulosic fibers or fiber mixes comprising cellulosic fibers. Fibers suitable for making the webs of this invention include: nonwood fibers, such as cotton fibers or cotton derivatives, abaca, kenaf, sabai grass, flax, esparto grass, straw, jute hemp, bagasse, milkweed floss fibers, and pineapple leaf fibers; and wood fibers such as those obtained from deciduous and coniferous trees, including softwood fibers, such as northern and southern softwood Kraft fibers; hardwood fibers, such as eucalyptus, maple, birch, aspen, or the like. Papermaking fibers used in connection with the invention are typically naturally occurring pulp-derived fibers (as opposed to reconstituted fibers such as lyocell or rayon) which are liberated from their source material by any one of a number of pulping processes familiar to one experienced in the art including sulfate, sulfite, polysulfide, soda pulping, etc. The pulp can be bleached if desired by chemical means including the use of chlorine dioxide, oxygen, alkaline peroxide and so forth. The products of the present invention may comprise a blend of conventional fibers (whether derived from virgin pulp or recycle sources) and high coarseness lignin-rich tubular fibers, such as bleached chemical thermomechanical pulp (BCTMP). Pulp-derived fibers thus also include high yield fibers such as BCTMP as well as thermomechanical pulp (TMP), chemithermomechanical pulp (CTMP) and alkaline peroxide mechanical pulp (APMP). "Furnishes" and like terminology refers to aqueous compositions including papermaking fibers, optionally wet strength resins, debonders and the like for making paper products.

Kraft softwood fiber is low yield fiber made by the well known Kraft (sulfate) pulping process from coniferous material and includes northern and southern softwood Kraft fiber, Douglas fir Kraft fiber and so forth. Kraft softwood fibers generally have a lignin content of less than 5 percent by weight, a length weighted average fiber length of greater than 2 mm, as well as an arithmetic average fiber length of greater than 0.6 mm.

Kraft hardwood fiber is made by the Kraft process from hardwood sources, i.e., eucalyptus and also has generally a lignin content of less than 5 percent by weight. Kraft hardwood fibers are shorter than softwood fibers, typically having a length weighted average fiber length of less than 1 mm and an arithmetic average length of less than 0.5 mm or less than 0.4 mm.

Recycle fiber may be added to the papermaking furnish in any amount. While any suitable recycle fiber may be used, recycle fiber with relatively low levels of ground wood is preferred in many cases, for example recycle fiber with less than 15% by weight lignin content, or less than 10% by weight lignin content may be preferred depending on the furnish mixture employed and the application. Recycle fiber is in many cases 80% hardwood fiber.

Zeta potential and titratable charge of the furnish are generally measured as described in U.S. Pat. No. 7,682,488 to Yeh et al. Details on both the electrophoretic mobility and titratable charge techniques can be found in Principles of Colloid and Surface Chemistry by P. Hiemenz and in Chapter 4: *Application of Electro kinetics in Optimization of Wet End Chemistry* in Wet Strength Resins and Their Application (L. Chan, Editor, 1994). In particular, a furnish slurry is tested for titratable charge with either a 0.001 N solution of PolyDADMAC or PVSK using a Mutek instrument as titratable charge detector. The salvageable components are recombined with the treated slurry and tested for zeta-potential with a Mutek SZP-10.

"Basesheet" refers to a unitary cellulosic sheet as manufactured by a paper machine. Basesheets may be layered; however, they have a unitary structure not readily delaminated. A "ply" of a finished product refers to basesheet incorporated into the product.

Unless otherwise specified, "basis weight", BWT, bwt, and so forth refers to the weight of a sheet product per specified area.

Consistency refers to percent solids of a nascent web, for example, calculated on a bone dry basis. A nascent web having 50 percent water and 50 percent bone dry pulp has a consistency of 50 percent.

"Air dry" or simply "dry" means including residual moisture, by convention up to about 10 percent moisture for pulp and up to about 6 percent for paper; while oven dry refers to pulp or paper which is dried in an oven for several hours and is significantly drier.

Products of the invention are made with a cellulosic fiber basesheet and have an absorbency or SAT value as well as tensiles and densities suitable for tissue and towel products. Typical SAT values are greater than about 3 g/g in most cases. See U.S. Pat. No. 8,778,138.

"CWP" refers to a process for making absorbent products by way of a conventional wet-press process; that is, wet-pressing a furnish to a drying cylinder with a papermaking felt followed by creping the web from the cylinder. See U.S. Pat. No. 7,951,266, FIG. 7 thereof.

A "Structured Basesheet Process" refers to a process for making an absorbent product by wet creping (fabric creping) from a cylinder prior to final drying. See U.S. Pat. Nos. 7,850,823; 7,585,388; 7,585,389; 7,662,257 and 7,399,378.

A "TAD Process" refers to through-air dried processes for making absorbent products. Throughdried, creped products are disclosed in the following patents: U.S. Pat. No. 3,994,771 to Morgan, Jr. et al.; U.S. Pat. No. 4,102,737 to Morton; and U.S. Pat. No. 4,529,480 to Trokhan. The processes described in these patents comprise, very generally, forming a web on a foraminous support, thermally pre-drying the web, applying the web to a Yankee dryer with a nip defined, in part, by an impression fabric, and creping the product from the Yankee dryer.

The absorbent characteristics of a product can be affected by the furnish, basis weight, strength, papermaking technology, and so forth. The sheet absorbency and converting technology for a specific product will impact the selection of bonding agent characteristics. CWP sheets are more consolidated than TAD sheets and therefore may have a lower wicking rate. Towel sheets commonly contain more softwood than tissue sheets, which may impact the pore size distribution of the web. It can be appreciated that an optimal bonding agent formula for one product may not be optimal for another.

Dry tensile strengths (MD or CD, which are the same for handsheets), stretch, ratios thereof, break modulus, stress and strain and other tensile characteristics are measured with a standard Instron test device or other suitable elongation tensile tester which may be configured in various ways, typically using 3 or 1 inch wide strips of tissue or towel, conditioned at 50% relative humidity and 23° C. (73.4), with the tensile test run at a crosshead speed of 2 in/min for modulus, 10 in/min for tensile. Wet tensile is measured by the Finch cup method or following generally the procedure for dry tensile, wet tensile is measured by first drying the specimens at 100° C. or so and then applying a 1½ inch band of water across the width of the sample with a Payne Sponge Device prior to tensile measurement. The latter method is referred to as the sponge method. The Finch cup method uses a three-inch wide strip of tissue that is folded into a loop, clamped in the Finch Cup, then immersed in water. The Finch Cup, which is available from the Thwing-Albert Instrument Company of Philadelphia, Pa., is mounted onto a tensile tester equipped with a 2.0 pound load cell with the flange of the Finch Cup clamped by the tester's lower jaw and the ends of tissue loop clamped into the upper jaw of the tensile tester. The sample is immersed in water that has been adjusted to a pH of 7.0.+/−0.1 and the tensile is tested after a 5 second immersion time. Tensile strengths are commonly expressed in units force per unit of width or simply in breaking length (BL) which is the tensile strength divided by the basis weight.

Wet/dry tensile ratios are simply ratios of the values determined by way of the foregoing methods. To express the ratio as a percent, it is multiplied by 100.

Tensile reduction is calculated relative to a control sample without debonder for purposes of comparison, i.e.: (Sample BL−ControlSamplew/o debonderBL)/(ControlSamplew/o debonder BL)×100%.

A towel product is typically characterized by having predominantly (more than 50% by weight based on fiber content) softwood fiber.

A tissue product is typically characterized by having predominantly (more than 50% by weight based on fiber content) hardwood fiber.

Water absorbency rate (WAR) is determined in accordance with TAPPI test method T 432 cm-99 or equivalent, for towel products using 0.1 mL of water and for tissue products using 0.01 mL of water. A shorter WAR time in seconds indicates faster water absorption by the absorbent paper.

Surfactants and Debonder/Softener Compositions

The ricinoleate-type surfactants and zwitterionic surfactants of the invention may be used along with conventional debonder and/or softener components, including conventional cationic surfactants if so desired. There is disclosed in U.S. Pat. No. 7,736,464 to Kokko a debonder composition including a combination of: (a) a quaternary ammonium surfactant component; and (b) a nonionic surfactant component, any of which may be used with the invention zwitterionic surfactants. The surfactants of the invention are most preferably used in debonder compositions along with a nonionic surfactant, for example those selected from the group consisting of alkoxylated fatty acids and alkoxylated fatty alcohols. Typically the nonionic surfactant includes the reaction product of a fatty acid or fatty alcohol with ethylene oxide such as a polyethylene glycol diester of a fatty acid (PEG mono or diols or PEG mono or diesters). One preferred composition which is used in connection with the present invention includes 15 wt % of imidazolinium zwitterion surfactants in a 1:1 mixture of PEG-400-mono and dioleates.

Other conventional debonder/softener components which may be used are disclosed in the following references: U.S. Pat. No. 5,622,597 to Callen et al.; U.S. Pat. No. 4,441,962 to Osborn, III and U.S. Pat. No. 4,351,699 also to Osborn, III; U.S. Pat. No. 5,698,076 to Phan et al.; U.S. Pat. No. 5,730,839 to Wendt et al.; U.S. Pat. No. 5,753,079 to Jenny et al.; U.S. Pat. No. 4,447,294 to Osborn, III; U.S. Pat. No. 5,279,767 to Phan et al. and U.S. Pat. No. 5,240,562 of Phan et al.

Debonder and or softener compositions may be applied to the sheet by any suitable method such as spraying or more typically by way of adding the debonder to the aqueous furnish in the headbox of a papermaking machine used to produce the sheet. In cases where a multilayer headbox is used to produce plies having multiple layers, treatment levels of debonder apply to any layer provided to the sheet. For example, if one layer has no added debonder (other than perhaps residual debonder in the water provided to the furnish) and another layer is treated at 4 lbs debonder/ton of papermaking fiber in the sheet, then the basesheet furnish is considered to be treated at a level of 4 lbs debonder/ton.

Charge density of the debonder composition is determined by any suitable technique. One procedure generally is seen in U.S. Pat. No. 8,852,399 to Neal et al., Cols. 51-52. Charge density is preferably measured using a Mutek titrator, or equivalent instrument. The charge density (charge demand) of the debonder composition herein is reported in meq/g units, determined as follows:

A Mutek PCD 05 Travel streaming current detector with titrator, deionized water, a top pan balance (capacity >400 gm), an auto pipetter with disposable tips or transfer pipettes, 250 ml beakers are used with the following reagents: PVSK Solution: Potassium salt of polyvinyl sulfate, 0.001 N, (BTG Americas Customer Support, 5085 Avalon Ridge PKWY, Norcross, Ga. 30071) or DADMAC Solution: Di-Allyl di-methyl ammonium chloride, 0.001 N, BTG Americas Customer Support, 5085 Avalon Ridge PKWY, Norcross, Ga. 30071). The procedure employed is:

1. Determine the solids content of the polymer that is to be analyzed for charge density (% solids A.R).
2. Weigh approximately 0.20-0.75 gm of the polymer (record the actual weight as gm. A.R.) into a 250 ml beaker, dilute with deionized water to make a 100 gm "stock solution". Mix thoroughly.
3. Weigh 5.00 gm of the stock solution into another 250 ml beaker and dilute to 100 gm with deionized water and mix well. This is your "working solution".
4. Weigh 10.00 gm of the working solution into the Mutek sample cup and turn on the Mutek. Wait 1-2 minutes until the streaming current potential has stabilized before starting the titration. (This is essential to get an accurate titration value.)
5. After noting the sign (+ or −) of the mV reading from the digital read out of the Mutek PCD, insert the appropriate burette tip (DADMAC for negatively charged solutions or PVSK for positively charged solutions) into the Mutek burette holder. Position the burette tip so that it touches the back inner wall of the sample cup. Do not immerse the tip in the sample.
6. Start the titration. When the titration has reached the endpoint the titrator will display the volume of titrant required to reach a "0 mV" reading. Record this titer value.

Sample Calculation:

$$\text{Charge Density (meq/gm)} = \frac{(\text{ml titer})(0.001\ \text{meq/ml})}{(10\ \text{gm working } sol.)(\text{gm } A.R./100\ \text{gm})(\%\ \text{solids } A.R./100\ \text{gm})(5\ \text{gm stock } sol./100\ \text{gm})}$$

Examples

A. Ricinoleate-Type Debonders

One preferred imidazolinium surfactant of the invention is represented:

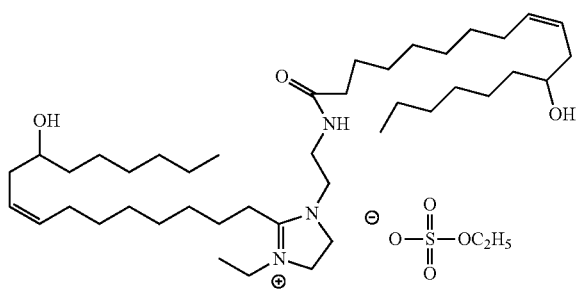 [SMILES: CCCCCCC(O)C/C=C\CCCCCCCC(=O)NCCN1CC[N+](CC)=C1CCCCCCC/C=C\CC(O)CCCCCC ; CCOS(=O)(=O)O]

This surfactant may be referred to as 3-ethyl-2-((Z)-11-hydroxyheptadec-8-en-1-yl)-1-(2-((Z)-12-hydroxyoctadec-9-enamido)ethyl)-4,5-dihydro-1H-imidazol-3-ium ethyl sulfate, or 3-ethyl-(2-(z)-11-hydroxyl-heptadec-8-en-1-yl)-1-(2-ricinoleamido ethyl)-4,5-dihydro-1H-imidazolinium ethyl sulfate, or 1-ethyl-2-((Z)-11-hydroxyheptadec-8-en-1-yl)-3-(2-((Z)-12-hydroxyoctadec-9-enamido)ethyl)-4,5-dihydro-1H-imidazol-3-ium ethyl sulfate. For present purposes, this surfactant is referred to simply as Ricin-IM+.

Synthesis Procedure

A reactor was charged with 57.25 g (0.186 mol) methyl ricinoleate, 9.55 g (0.093 mol) diethylenetriamine (DETA) and heated under argon atmosphere with stirring to 160° C., whereupon methanol began to reflux. Enough methanol was distilled off to bring the temperature to 180° C.; stirring with argon sparging was continued for 2 days to yield pure 3-(2-(z)-11-hydroxyl-hepatadec-8-en-1-yl)-1-(2-ricinoleamido ethyl)-4,5-dihydro-1-H-imidazoline (Ricin-Im) as a viscous light straw-colored fluid. $^{13}$C NMR (CDCl$_3$, 100 MHz) δ 25.8, 36.6, 38.0, 46.6, 50.2, 52.2, 167.5, 173.4 ppm. A flask was charged with 6.461 g (0.01 mol) Ricin-Im, 1.542 g (0.01 mol) diethyl sulfate, and 20 ml anhydrous N-Methyl-2-pyrrolidone (NMP), heated under an argon atmosphere with stirring at 140° C. for 2 days. The mixture was evaporated under vacuum (90° C./0.8 mmHg) to remove the solvent. Yield of the final product (Ricin-Im+) was over 90%. $^{13}$C NMR (CDCl$_3$, 100 MHz) δ 175, 168.3, 47.5, 46.9, 46.7, 42.2, 36.3, 36.1, 25.7, 23.9, 12.7 ppm. The synthesis is shown schematically below:

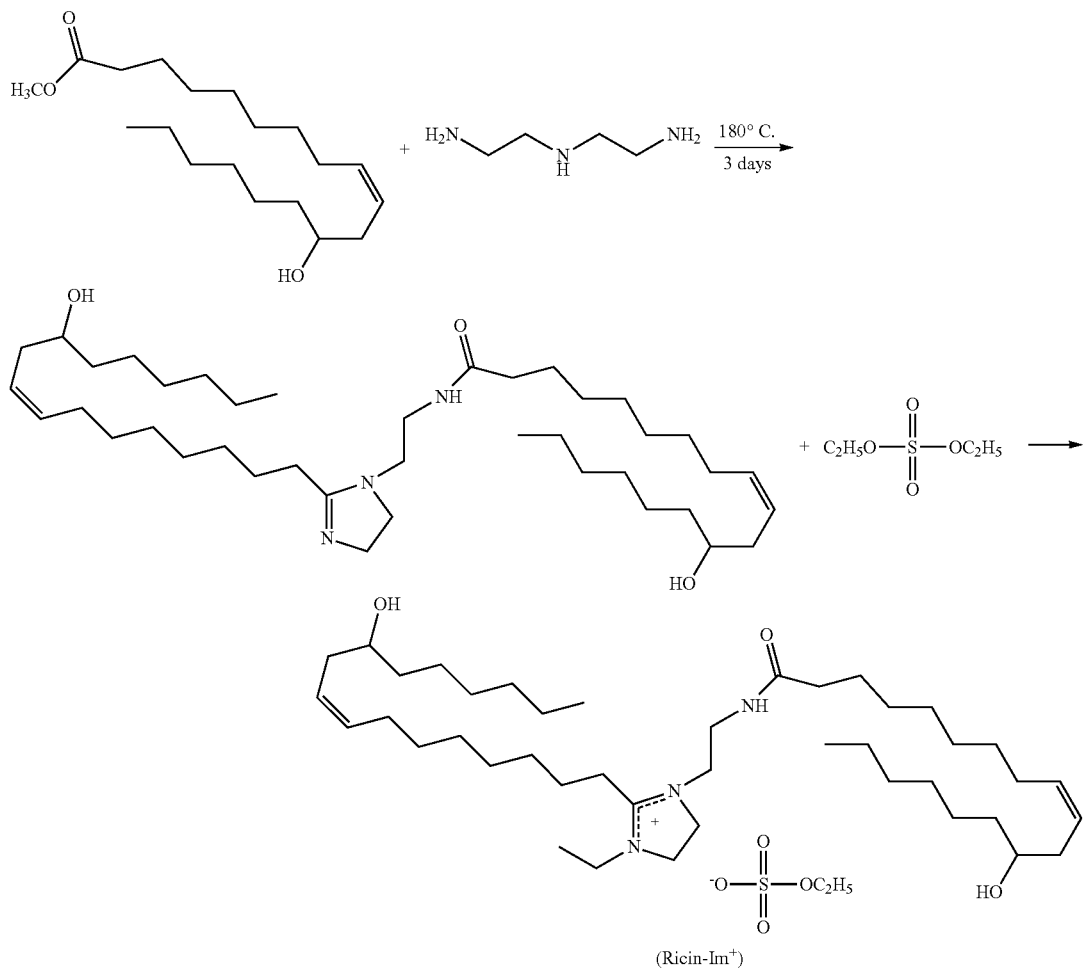

15 wt. % Ricin-Im+ was incorporated into PEG-400-monoleate in order to formulate a debonder composition of the invention, DBRIm+ for evaluation. For purposes of comparison, a corresponding imidazolinium surfactant made with oleate instead of ricinoleate was incorporated into PEG-400-monoleate in order to formulate a debonder composition, CDBIm+.

Charge density of DBRIm+ was only 0.16 meq/g, while that of CDBIm+ was 0.32 meq/g, although the cationic imidazolinium in both DBRIm$^+$ and CDBIm$^+$ is 15 wt %. Interestingly, a previous ricin imidazolinium debonder formulation of 10 wt % of cationic imidazolinium in PEG-400 monooleate also showed a 0.16 meq/g charge density. It may be that ricin imidazolinium debonders form different micelle structure compared to oleate imidazolinium debonders such as CDBIm$^+$.

In order to prepare a towel-type handsheet, a 15 g (O.D. wt.) sample of an unrefined 65:35 mixture of softwood and hardwood furnish is diluted to 1500 ml using tap water, a given dosage of DBRIm$^+$ and CDBIm$^+$ was added and stirred 5 min. 10 #/T Amres® 1110E was added and mixed for 5 minutes. The samples were tested for titratable charge by titration with either a 0.001 N solution of PolyDADMAC or PVSK using a Mutek instrument as detector.

The salvageable components were recombined with the treated slurry and tested for zeta-potential with a Mutek SZP-10, diluted to 15 L and the pH adjusted to around 8. The material was formed into British handsheets, pressed at 15 psi for 5 min, and dried on rotating dryer drum at 250° F., then treated in an oven at 105° C. for 5 minutes. Details appear in Table 1.

Table 1 shows the titratable charges, zeta potentials of the slush and the effect of two debonders (DBRIm$^+$ and CDBIm$^+$) in the towel type handsheet prepared as above. Both titratable charge and zeta potential of slush with DBRIm$^+$ were better controlled compared to those of the slush with CDBIm$^+$. For example, the titratable charge and zeta potential of the slush with CDBIm$^+$ kept positive and increased steadily, while those values of slush with DBRIm$^+$ were stable. Carboxymethyl cellulose (CMC) was usually required on a paper machine to balance the positive net charge. Since DBRIm$^+$ impacts the net charge in the headbox less than conventional debonder, less CMC is required for balancing charge, and one or both of softness and wet/dry tensile can be improved.

Figure 2:
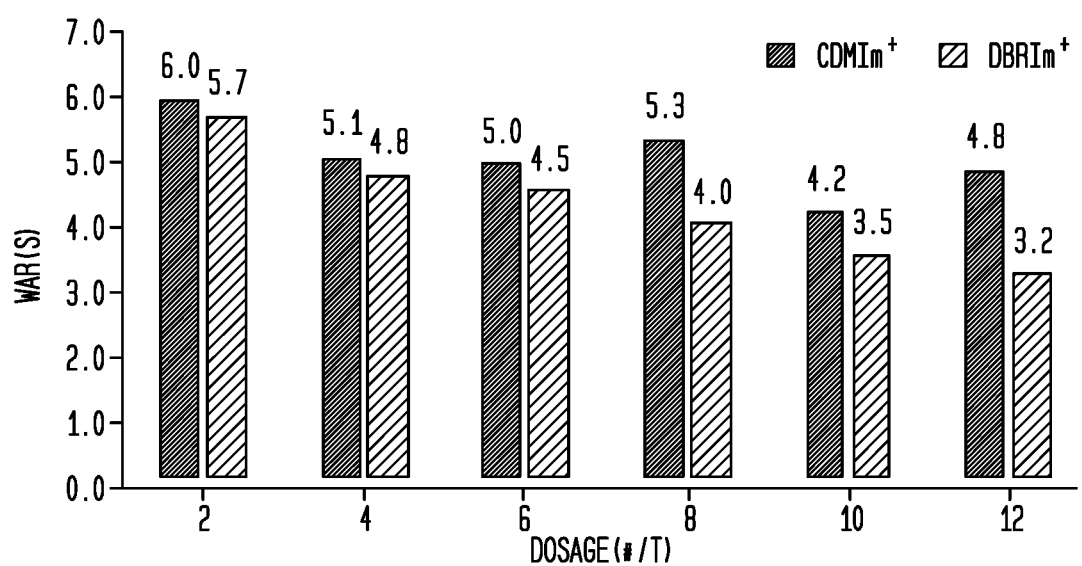
FIG. 2 is a histogram of Water Absorbancy Rate (WAR) for towel-type handsheets made with debonder compositions DBRIm⁺ and CDBIm⁺ at various debonder dosage levels.

FIG. 2 shows the WAR of the handsheet dosed with debonder and Amres® 1110E. The WAR of the handsheets made with DBRIm$^+$ improved 5-33% compared to that of handsheets made with CDBIm$^+$, showing that the hydrophilic substitution on the debonder likely improves absorbency capacity as well.

Figure 3:
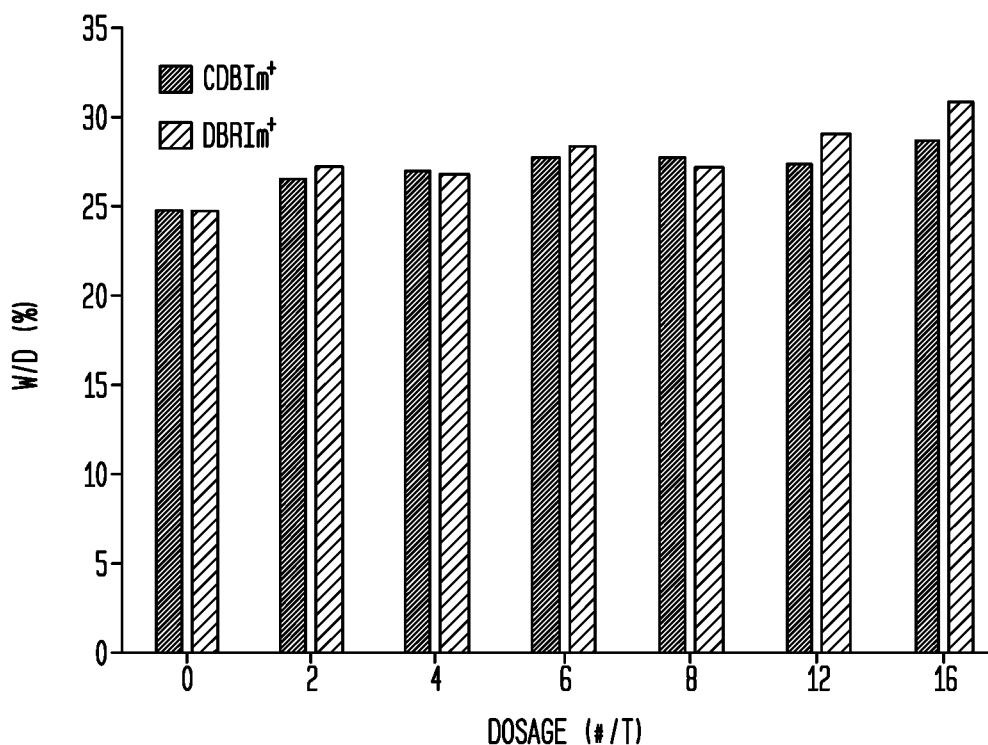
FIG. 3 is a histogram illustrating wet/dry tensile ratios of towel-type handsheets made with debonder compositions DBRIm⁺ and CDBIm⁺ at various debonder dosage levels.

The wet/dry tensile of DBRIm$^+$ dosed handsheets showed no significant difference compared to those dosed with cationic debonder CDBIm$^+$ under the conditions tested in Table 1. (FIG. 3).

In another series of experiments directed to tissue-type handsheets, a 15 g (O.D. wt.) sample of an unrefined 35:65 mixture of softwood and hardwood furnish was diluted to 1500 ml using tap water, adjusted to pH 5-5.5, and a given dosage of DBRIm$^+$ or CDBIm$^+$ was added. The mixture stirred 5 min. The slurry was tested for titratable charge with either a 0.001 N solution of PolyDADMAC or PVSK using a Mutek instrument as a titratable charge detector. The salvageable components were recombined with the treated slurry and tested for zeta-potential with a Mutek SZP-10. The slurry was then diluted to 15 L, pH adjusted to 5-5.5, and the slurry was formed into 1.0 gm British handsheets, pressed at 15 psi for 5 min, and dried on a rotating dryer drum at 250° F. Details appear in Table 2.

Figure 4:
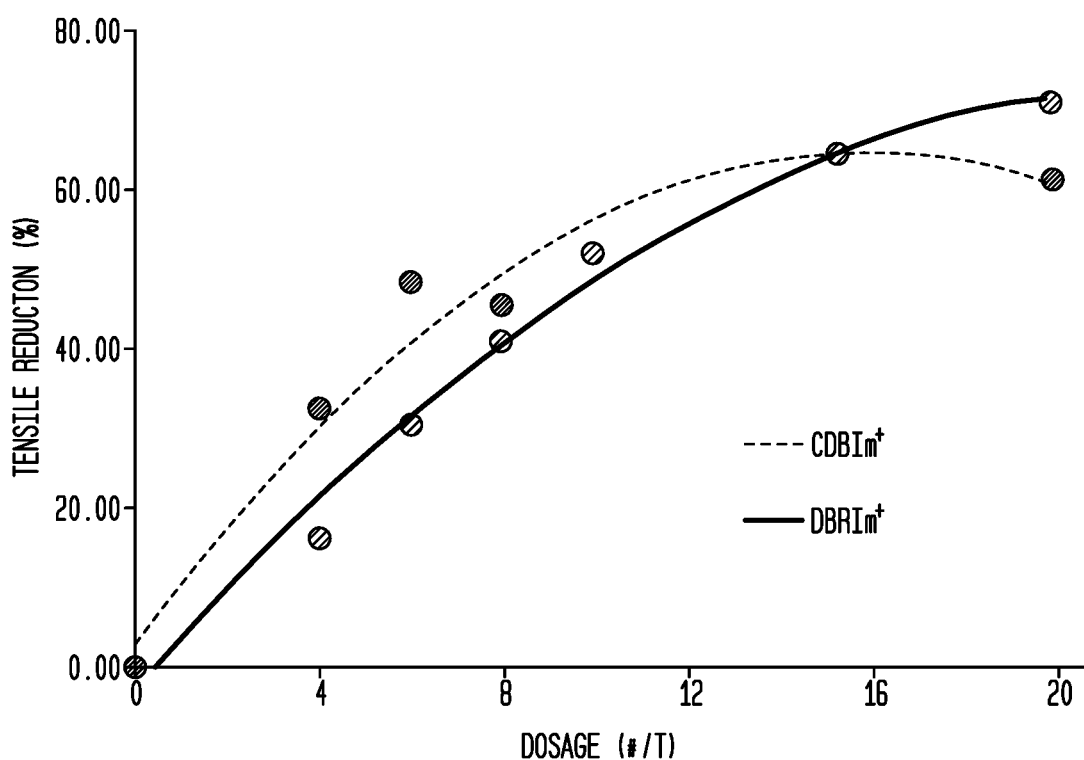
FIG. 4 is a plot of tensile reduction versus debonder dosage levels for tissue-type handsheets made with debonder compositions DBRIm⁺ and CDBIm⁺.

Table 2 shows the titratable charges, zeta-potentials of the slush and dry tensile property of the tissue type handsheet. At the same debonder dosage, the zeta potential of DBRIm$^+$ is lower than that of CDBIm$^+$, which indicates the surface of the fiber was saturated slower when DBRIm$^+$ was dosed due to its lower charge density. As shown in FIG. 4, the tensile reduction of DBRIm$^+$ was lower than that of CDBIm$^+$ at low debonder dosage, due to higher charge density CDBIm$^+$ which was absorbed faster onto the fiber. When the dosage increased, tensile reduction of the handsheet dosed with DBRIm$^+$ began to catch up and eventually exceeded that of

TABLE 1

Charge and Tensile Properties of DBRIm$^+$ and CDBIm$^+$ in Towel Type Handsheet

| Sample ID | Debonder | Dose (#/t) | Titratable Charge (ml/10 ml) | Zeta Potential (mV) | Dry Breaking Length (Km) | Wet Breaking Length (Km) | W/D % | W.A.R (0.1 mL) s |
|---|---|---|---|---|---|---|---|---|
| 1 | Blank | 0 | 0.03 | 45.0 | 2.32 | 0.58 | 25 | N/A |
| 2 | DBRIm$^+$ | 2 | −0.04 | 48.2 | 2.18 | 0.60 | 27 | 5.7 |
| 3 | | 4 | 0.04 | 55.4 | 2.10 | 0.57 | 27 | 4.8 |
| 4 | | 6 | 0.04 | 47.6 | 1.82 | 0.52 | 29 | 4.5 |
| 5 | | 8 | 0.04 | 43.8 | 1.72 | 0.47 | 27 | 4.0 |
| 6 | | 12 | −0.02 | 41.6 | 1.41 | 0.41 | 29 | 3.5 |
| 7 | | 16 | 0.03 | 45.9 | 1.17 | 0.36 | 31 | 3.2 |
| 8 | CDBIm$^+$ | 2 | 0.04 | 54.3 | 2.24 | 0.60 | 27 | 6.0 |
| 9 | | 4 | 0.05 | 56.7 | 2.12 | 0.58 | 27 | 5.1 |
| 10 | | 6 | 0.06 | 54.7 | 1.92 | 0.53 | 28 | 5.0 |
| 11 | | 8 | 0.09 | 52.5 | 1.82 | 0.51 | 28 | 5.3 |
| 12 | | 12 | 0.1 | 51.8 | 1.71 | 0.47 | 27 | 4.2 |
| 13 | | 16 | 0.15 | 53.7 | 1.71 | 0.49 | 29 | 4.8 |

Furnish = HW/SW dry lap (35/65) Debonder was dosed prior, 10#/T Amres ® 1110E

As shown in FIG. 1, while synergistically applied with Amres® 1110E, the dry tensile reduction of the handsheets with DBRIm$^+$ outperformed handsheets with CDBIm$^+$ in the whole dose range. DBRIm$^+$ had a better retention than CDBIm$^+$ when synergistically applied with Amres® 1110E.

CDBIm$^+$. At #/T dosage of DBRIm$^+$, the tensile reduction reached 71.4%, while zeta-potential of the furnish kept negative. Furnish with CDBIm$^+$ above 15#/T dosage exhibited cationic zeta-potential without the addition of any other chemistries.

TABLE 2

Charge and Tensile Properties of DBRIm⁺ and CDBIm⁺ in Tissue Type Handsheet without Strength Resin

| Sample ID | Debonder | Dose (#/t) | Titratable Charge (ml/10 ml) | Zeta Potential (mV) | Dry Breaking Length (Km) | Dry Tensile Reduction |
|---|---|---|---|---|---|---|
| 1 | Blank | 0 | −0.1 | −64.3 | 1.59 | 0 |
| 2 | DBRIm⁺ | 4 | −0.01 | −67.3 | 1.34 | 16 |
| 3 | | 6 | −0.06 | −52.2 | 1.11 | 31 |
| 4 | | 8 | 0.02 | −42.3 | 0.94 | 41 |
| 5 | | 10 | 0.06 | −28.4 | 0.76 | 52 |
| 6 | | 15 | 0.06 | −23.7 | 0.56 | 65 |
| 7 | | 20 | 0.08 | −10.5 | 0.46 | 71 |
| 8 | CDBIm⁺ | 4 | −0.06 | −50.5 | 1.07 | 33 |
| 9 | | 6 | −0.06 | −37.2 | 0.82 | 49 |
| 10 | | 8 | 0.05 | −8.0 | 0.86 | 46 |
| 11 | | 10 | 0.04 | −7.2 | 0.76 | 52 |
| 12 | | 15 | 0.07 | 14.9 | 0.55 | 65 |
| 13 | | 20 | 0.04 | 26.3 | 0.61 | 61 |

Furnish = HW/SW dry lap (65/35)

B. Zwitterionic Imidazolinium Debonders

Synthesis Examples

1. 4-(2-((Z)-heptadec-8-en-1-yl)-1-(2-oleamidoethyl)-4,5-dihydro-1H-imidazol-3-ium-3-yl)butane-1-sulfonate, Compound 1 (z-IM-3)

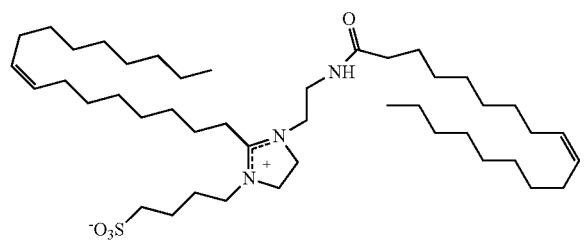

A reactor was charged with 54.89 g (0.186 mol) methyloleate, 9.55 g (0.093 mol) diethylenetriamine and heated under an argon atmosphere with stirring to 160° C., whereupon methanol began to reflux, enough methanol was distilled off to bring to 180° C., stirring with argon sparging was continued for 2 days to yield pure 3-(2-((z)-hepatadec-8-en-1-yl)-1-(2-oleamido ethyl)-4,5-dihydro-1H-imidazoline (Im) as a viscous light straw colored fluid. $^{13}$C NMR (CDCl$_3$, 100 MHz) δ=25.8, 36.6, 38.0, 46.6, 50.2, 52.2, 167.5, 173.4. A flask was charged with 6.14 g (0.01 mol) 3-(2-((z)-hepatadec-8-en-1-yl)-1-(2-oleamido ethyl)-4,5-dihydro-1H-imidazoline, 1.36 g (0.01 mol) 1,4-butane sultone, and 20 ml anhydrous N-Methyl-2-pyrrolidone (NMP), heated under an argon atmosphere with stirring at 140° C. for 2 days. Evaporated the mixture in vacuo (90° C./0.8 mmHg). A viscous dark amber wax like solid comprised of more than 90 wt % of 4-(2-((Z)-heptadec-8-en-1-yl)-1-(2-oleamidoethyl)-4,5-dihydro-1H-imidazol-3-ium-3-yl)butane-1-sulfonate (z-Im-3) was obtained. $^{13}$C NMR (CDCl$_3$, 100 MHz), δ=25.6, 36.0, 36.4, 46.5, 47.0, 47.4, 47.6, 50.1, 168.5, 174.8. The compound was obtained at high yield (>90%). This compound formed stable debonder compositions with nonionic surfactants such as PEG oleates.

2. 3-(2-((Z)-heptadec-8-en-1-yl)-1-(2-oleamidoethyl)-4,5-dihydro-1H-imidazol-3-ium-3-yl)propane-1-sulfonate, Compound 2 (z-Im-2)

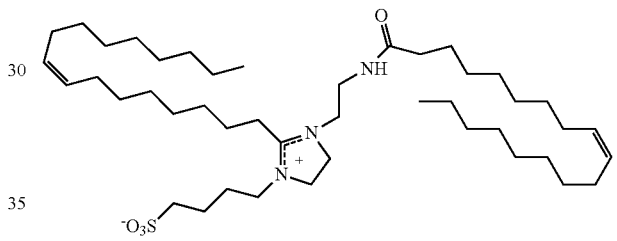

was prepared following the procedure of Example 1, substituting 1,3-propane sultone for butane sultone. The compound was obtained at high yield (>90%). This compound formed stable debonder compositions with nonionic surfactants such as PEG oleates.

3. 2-(2-((Z)-heptadec-8-en-1-yl)-1-(2-oleamidoethyl)-4,5-dihydro-1H-imidazol-3-ium-3-yl)ethane-1-sulfonate, Compound 3 (z-IM-1)

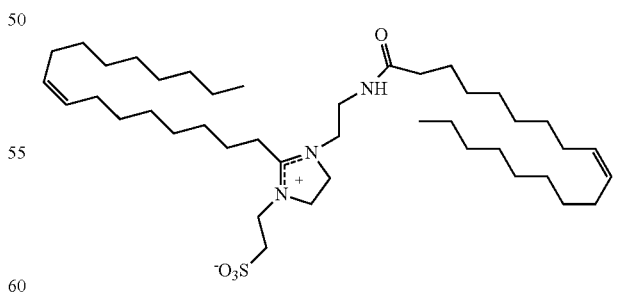

A reactor was charged with 54.89 g (0.186 mol) methyloleate, 9.55 g (0.093 mol) diethylenetriamine and heated under an argon atmosphere with stirring to 160° C., whereupon methanol began to reflux, enough methanol was distilled off to bring to 180° C., stirring with argon sparging was continued for 2 days to yield pure 3-(2-((z)-heptadec-8-en- 1-yl)-1-(2-oleamido ethyl)-4,5-dihydro-1H-imidazoline as a viscous light straw colored fluid. $^{13}$C NMR (ppm in CDCl$_3$, 100 MHz) δ=25.8, 36.6, 38.0, 46.6, 50.2, 52.2, 167.5, 173.4. A flask was charged with 4.000 g (6.514 mmol) 3-(2-((z)-heptadec-8-en-1-yl)-1-(2-oleamido ethyl)-4,5-dihydro-1H-imidazoline, 1.648 g (7.810 mmol) sodium 2-bromoethyl-sulfonate, 20 ml anhydrous N-Methyl-2-pyrrolidone (NMP), heated under an argon atmosphere with stirring at 140° C. for 2 days. Evaporated the mixture in vacuo (90° C./0.8 mmHg), poured into 30 mL sodium chloride saturated deionized water, extracted with 20 mL aliquots of chloroform until the chloroform layer had only a faint color, combined the chloroform layer and dried over anhydrous magnesium sulfate, filtered through celite, vacuum distilled. A viscous dark amber fluid comprised of about 38 wt % of 2-(2-((Z)-heptadec-8-en-1-yl)-1-(2-oleamidoethyl)-4,5-dihydro-1H-imidazol-3-ium-3-yl)ethane-1-sulfonate (z-Im-1), 48 wt % Im and 15 wt % of NMP was obtained. The product was purified using flash chromatography with MeOH-water (9:1), and yield 80 mol % of z-IM-1. $^{13}$C NMR (ppm in CDCl$_3$, 100 MHz) δ=170.8, 46.7, 47.4, 36.0, 46.3, 174.8, 25.7, 43.4, 45.7, 362, 25.6.

Zwitterionic Imidazolinium Debonder Testing

Debonders were formulated with Compound 1 (z-IM-3) and Compound 2 (z-IM-2) by admixing 15 wt. % of these surfactants into PEG-400 monooleate. The debonder composition formulated with Compound 1 is identified herein and in the appended Figures as DBC1 and, while the debonder composition formulated with Compound 2 is referred to herein and in the appended Figures as DBC2. A Control debonder, CDB, was formulated with 15 wt. % of the corresponding imidazolinium salt, this control surfactant having the same structure except for the alkyl sulfonate substitution. DBC1 has a charge density of −0.05 meq/g while the control debonder composition has a positive charge density which is considerably higher.

Handsheet experiments were designed to determine the performance of zwitterionic-type debonders when dosed with permanent wet strength resin (pWSR) or temporary wet strength resin (tWSR) as follows: 1. debonder added with PAE type pWSR (Amres® 1100E) and 2. debonder added with cationic type tWSR (Kemira Fennorez® 110). The debonder formulations DBC1, DBC2 and the Control CDB were directly compared in handsheets over a dosage range of 0-8 lb as-received formulation/T. Freshly prepared 1 wt % water solutions of a given dosage of DBC1, DBC2 and the Control CDB were used.

In a first series of experiments a given 10.00 g (oven dry weight) sample of an unrefined 65:35 mixture of softwood and hardwood furnish was suspended in 300 mL of tap water, a given dosage of DBC1, DBC2 or Control CDB was added after given dosage of Amres® 1100E (10 #/T) and stirred 5 min, tested for titratable charge by titration with either a 0.001 N solution of poly(diallyldimethylammonium chloride) (PDADMAC) or poly(vinylsulfate potassium) (PVSK) using a Mutek PCD-03 instrument as detector. The salvageable components were recombined with the treated slurry, diluted to 600 mL and tested for zeta-potential with a Mutek SZP-10 zeta potential meter. The furnish was diluted to 8.0 L, formed into British handsheets, pressed at 15 psi for 5 min, and dried on rotating dryer drum at 250° F.

In a second series of experiments, a given 10.00 g (O.D. wt.) sample of an unrefined 65:35 mixture of softwood and hardwood furnish was suspended in 300 mL of tap water, a given dosage of DBC1, DBC2 or Control CDB was added before given dosage of Amres® 1100E (10 #/T) and stirred 5 min, tested for titratable charge by titration with either a 0.001 N solution of PDADMAC or PVSK using a Mutek PCD-03 instrument as detector. The salvageable components were recombined with the treated slurry, diluted to 600 mL and tested for zeta-potential with a Mutek SZP-10 zeta potential meter. The furnish was diluted to 8.0 L, formed into British handsheets, pressed at 15 psi for 5 min, and dried on rotating dryer drum at 250° F.

In a third series of experiments, a given 10.00 g (O.D. wt.) sample of an unrefined 35:65 mixture of softwood and hardwood furnish was suspended in 300 mL of tap water, a given dosage of DBC1, DBC2 or Control CDB was added after given dosage of Kemira Fennorez 110 (7 #/T) and stirred 5 min, tested for titratable charge by titration with either a 0.001 N solution of PDADMAC or PVSK using a Mutek PCD-03 instrument as detector. The salvageable components were recombined with the treated slurry, diluted to 600 mL and tested for zeta-potential with a Mutek SZP-10 zeta potential meter. The furnish was diluted to 8.0 L, formed into British handsheets, pressed at 15 psi for 5 min, and dried on rotating dryer drum at 250° F.

Results, including titratable charge and zeta potential of the furnish, as well as tensile properties of the handsheets, appear in Tables 3, 4, 5 and are summarized in the discussion which follows and the attached Figures.

a. Debonder Addition after Amres® 1100E.

In Table 3, Sample 1 is the reference which was dosed only by Amres® 1100E (10 #/T), both titratable charge and zeta potential were positive, which implies the fibers had become cationic after Amres® 1100E (10 #/T) dosing. When the pulp slurry was dosed with Amres® 1110E (10 #/T) prior to the zwitterion debonder dose, the titratable charge of the zwitterion debonder cells remained the same (slightly negative) as the dose was increased, while the titratable charge of Control CDB cell kept positive and increasing. The zeta potentials decreased as the zwitterion debonder doses increased. This implies that anionic zwitterion debonder was being retained on the fibers. Table 3 shows the titratable charges, zeta-potentials and handsheet properties.

Tensile reduction is calculated relative to Sample 1 (no debonder) in each of the three trials: (Sample BL−Sample 1BL)/(Sample 1BL)×100%.

TABLE 3

Debonder added after Amres ® 1100E.

| Sample ID | Debonder | Dose (#/T) | Titratable Charge (ml/10 ml) | Zeta Potential (mV) | Basis Weight (gm/m$^2$) | Dry Breaking Length (Km) | Wet Breaking Length (Km) | W/D |
|---|---|---|---|---|---|---|---|---|
| 1 | | 0 | 0.03 | 44 | 52.74 | 2.13 | 0.54 | 0.25 |
| 2 | DBC2 | 2 | −0.03 | 34 | 54.14 | 1.90 | 0.49 | 0.26 |
| 3 | | 4 | −0.03 | 29 | 53.72 | 1.63 | 0.43 | 0.26 |
| 4 | | 6 | −0.03 | 27 | 53.51 | 1.39 | 0.38 | 0.27 |

TABLE 3-continued

Debonder added after Amres ® 1100E.

| Sample ID | Debonder | Dose (#/T) | Titratable Charge (ml/10 ml) | Zeta Potential (mV) | Basis Weight (gm/m$^2$) | Dry Breaking Length (Km) | Wet Breaking Length (Km) | W/D |
|---|---|---|---|---|---|---|---|---|
| 5 | | 8 | −0.04 | 23 | 54.66 | 1.22 | 0.34 | 0.28 |
| 7 | DBC1 | 2 | −0.02 | 33 | 52.84 | 1.88 | 0.48 | 0.26 |
| 8 | | 4 | −0.04 | 29 | 53.93 | 1.56 | 0.44 | 0.28 |
| 9 | | 6 | −0.03 | 26 | 53.64 | 1.39 | 0.37 | 0.27 |
| 10 | | 8 | −0.04 | 23 | 53.68 | 1.14 | 0.32 | 0.28 |
| 12 | CDB | 2 | 0.06 | 46 | 53.82 | 2.00 | 0.51 | 0.26 |
| 13 | | 4 | 0.07 | 45 | 54.60 | 1.79 | 0.44 | 0.25 |
| 14 | | 6 | 0.08 | 46 | 54.71 | 1.51 | 0.41 | 0.27 |
| 15 | | 8 | 0.11 | 48 | 54.12 | 1.46 | 0.37 | 0.25 |

Figure 5:
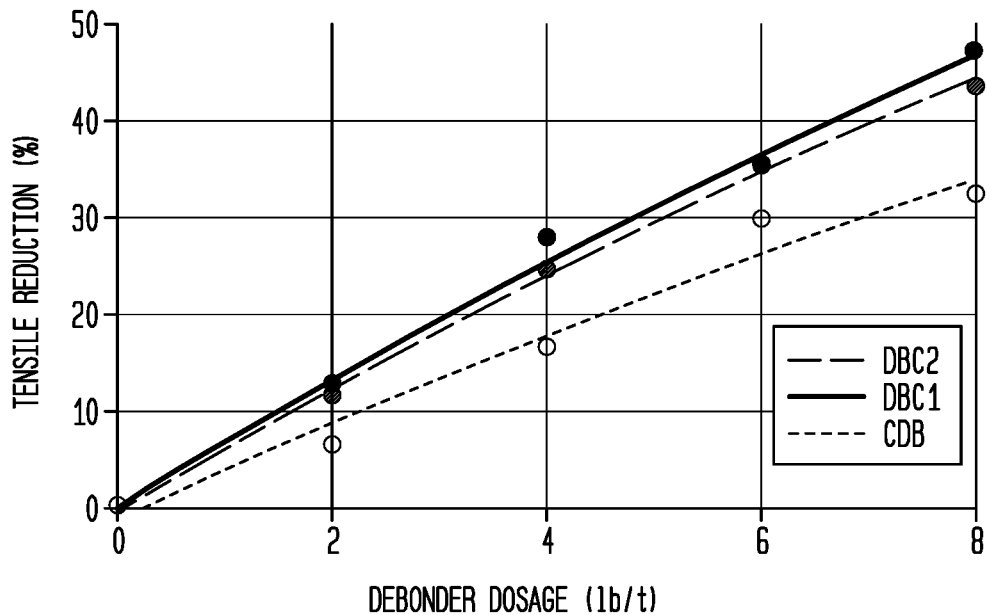
FIG. 5 is a plot of tensile reduction versus debonder dosage for handsheets, wherein the furnish was treated with cationic permanent wet strength resin prior to adding debonder.
Figure 6:
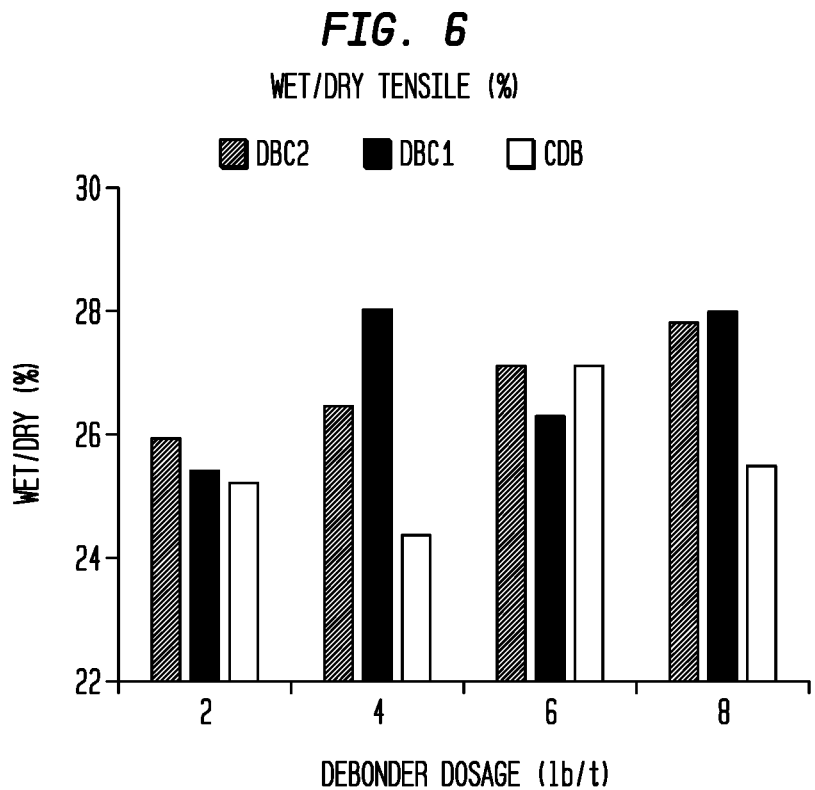
FIG. 6 is a histogram of wet/dry tensile ratios for handsheets, wherein the furnish was treated with cationic permanent wet strength resin prior to adding debonder.

Furnish = HW/SW dry lap (35/65)
All samples dosed with 10 #/T Amres ® 1110E prior to debonder addition FIGS. 5 and 6 show the tensile reduction and wet/dry tensile vs. debonder dosage. Both zwitterion debonder formulations DBC1 and DBC2 showed improved tensile reduction compared to the Control debonder over the whole dosage range, which implies zwitterion debonders had a better retention rate compared to the Control cationic debonder if we dosed Amres® 1100E prior to debonder. Zwitterion debonders showed an anionic property believed to be due to the strongly acidic nature of sulfonic acid (the conjugate acid of the sulfonate moiety present in the zwitterion), and interacted better with the fibers which became cationic after Amres® 1100E dosed. The cationic Control debonder, competed with cationic WSR on the fiber, lowered its retention rate and impaired debond performance. Zwitterion debonders also showed similar or better W/D compared to the Control debonder.

b. Debonder Addition Before Amres® 1100E.

When the pulp slurry was dosed with Amres® 1110E (10 #/T) after the zwitterion debonder dose, the titratable charge of the zwitterion debonder cells decreased as the dose was increased, while the titratable charge of the Control debonder cell kept increasing. The zeta potentials in the zwitterion debonder cells decreased as the zwitterion debonder doses increased, while the zeta potential of the Control debonder cell increases as debonder dosage increased; as shown in Table 4.

Figure 7:
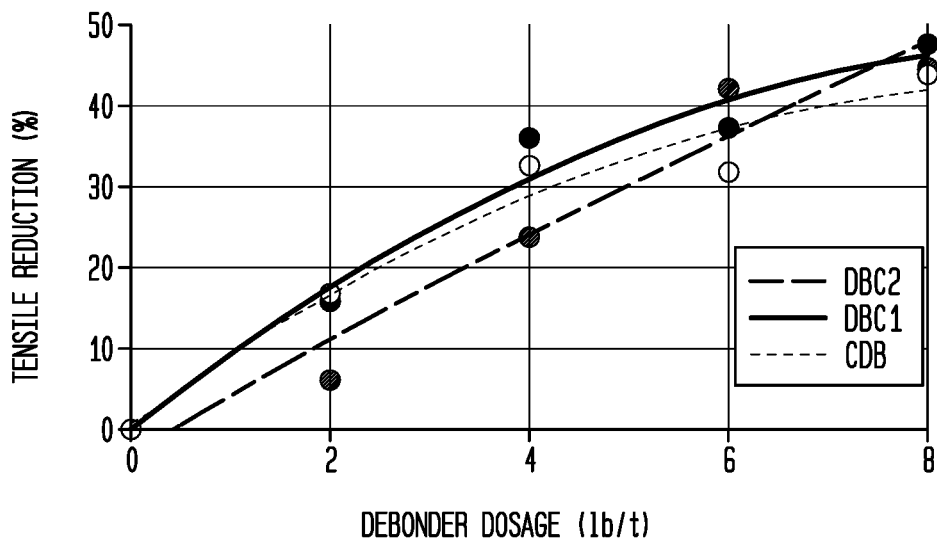
FIG. 7 is a plot of tensile reduction versus debonder dosage for handsheets, wherein the furnish was treated with cationic permanent wet strength resin after adding debonder.
Figure 8:
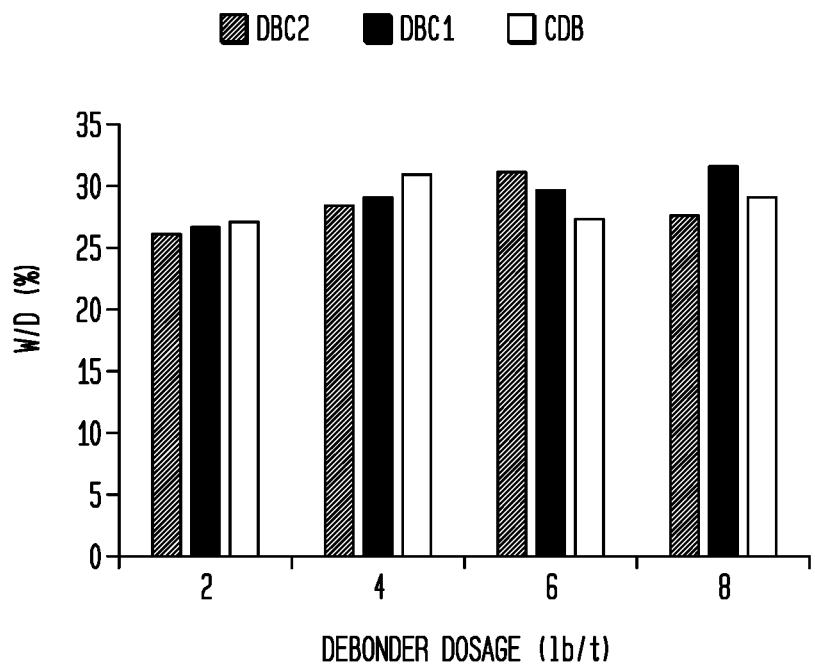
FIG. 8 is a histogram of wet/dry tensile ratios for handsheets, wherein the furnish was treated with cationic permanent wet strength resin after adding debonder.

FIGS. 7 and 8 show the tensile reduction and wet/dry tensile vs. debonder dosage. DBC1 showed similar tensile reduction at lower dosage compared to the Control debonder, but outperformed the Control debonder at higher dosage. DBC2 didn't perform as well as the Control debonder at low dosage, but became better at higher dosage. Wet/Dry tensile didn't show significant difference between zwitterion debonders and Control debonder cells.

Figure 9:
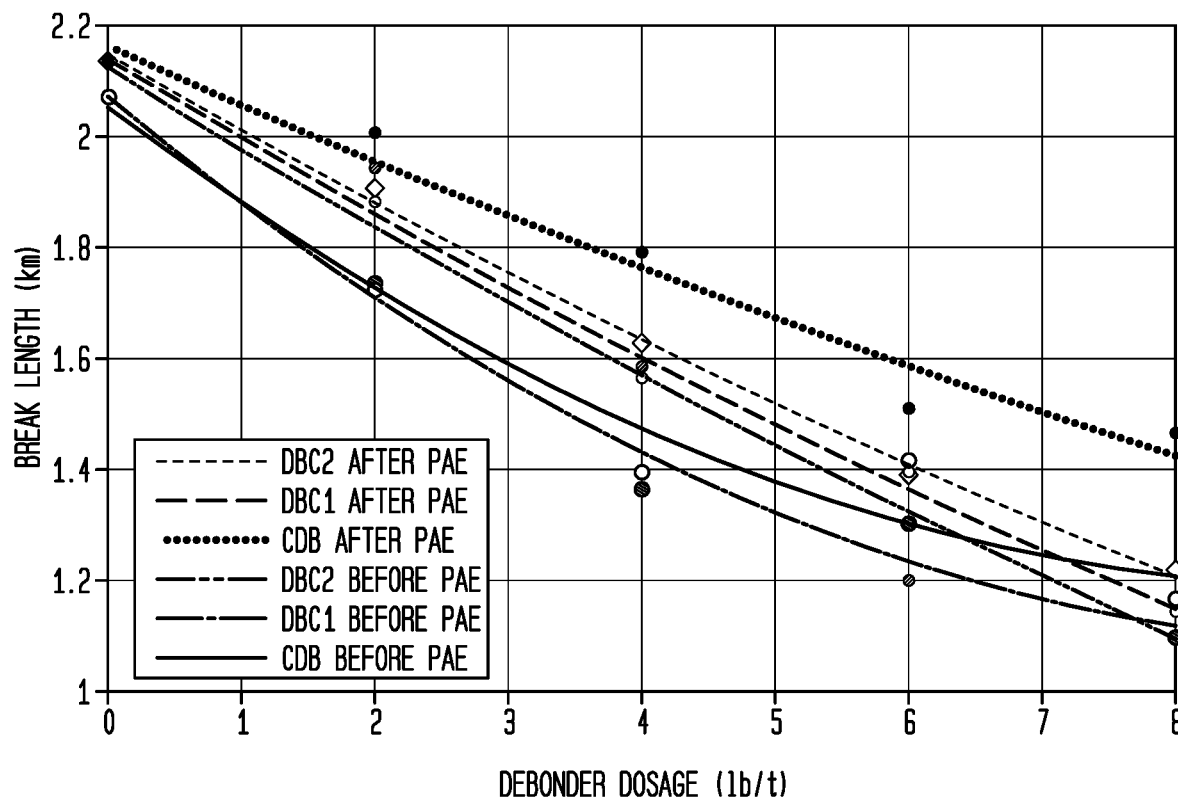
FIG. 9 is a plot of dry breaking length versus debonder dosage for various products.

It is important to consider the adding sequence of pWSR and debonders. If pWSR were added prior to debonder, the anionic fiber would be saturated by cationic pWSR and built higher dry strength compared to adding pWSR after debonder at the same pWSR dosage. In FIG. 9, the Control debonder after PAE showed highest dry strength over the whole dosage range due to the pre-built strength by adding WSR first and lower retention rate of cationic debonder. Both DBC1 and DBC2 showed better debond performance than the Control debonder when they were all added after WSR, which indicates DBC2 and DBC1 controlled the stock charge better and were retained more in the handsheets. When debonders were added prior to WSR, DBC1 debonded better than the Control debonder and DBC2. The wet/dry tensile of zwitterion debonders dosed handsheets showed no significant difference compared to those dosed with the Control cationic debonder.

To improve the strength of handsheets, WSR should be added first, then add debonder to provide some softness. In

TABLE 4

Debonder added before Amres ® 1100.

| Sample ID | Debonder | Dose (#/T) | Titratable Charge (ml/10 ml) | Zeta Potential (mV) | Basis Weight (gm/m$^2$) | Dry Breaking Length (Km) | Wet Breaking Length (Km) | W/D |
|---|---|---|---|---|---|---|---|---|
| 1 | | 0 | 0.08 | 45 | 53.69 | 2.07 | 0.51 | 0.25 |
| 2 | DBC2 | 2 | 0.15 | 41 | 53.19 | 1.94 | 0.51 | 0.26 |
| 3 | | 4 | 0.09 | 40 | 52.81 | 1.58 | 0.45 | 0.28 |
| 4 | | 6 | 0.08 | 37 | 53.31 | 1.20 | 0.37 | 0.31 |
| 5 | | 8 | 0.06 | 35 | 53.84 | 1.16 | 0.32 | 0.28 |
| 7 | DBC1 | 2 | 0.15 | 40 | 53.13 | 1.73 | 0.46 | 0.27 |
| 8 | | 4 | 0.08 | 37 | 54.09 | 1.36 | 0.4 | 0.29 |
| 9 | | 6 | 0.06 | 35 | 53.36 | 1.30 | 0.39 | 0.30 |
| 10 | | 8 | 0.07 | 39 | 53.16 | 1.10 | 0.35 | 0.32 |
| 12 | CDB | 2 | 0.09 | 49 | 53.11 | 1.72 | 0.47 | 0.27 |
| 13 | | 4 | 0.08 | 49 | 53.4 | 1.39 | 0.43 | 0.31 |
| 14 | | 6 | 0.11 | 50 | 53.94 | 1.41 | 0.39 | 0.28 |
| 15 | | 8 | 0.15 | 51 | 54.6 | 1.17 | 0.34 | 0.29 |

Furnish = HW/SW dry lap (35/65)
All samples dosed with 10 #/t Amres ® 1110E after debonder addition this case, zwitterion debonder debonded better than the Control cationic debonder. Adding debonder first could improve the debond performance. Cationic debonder would consume the anionic sites on the fiber first, which may lower the retention rate of WSR and therefor decrease the tensile of the handsheets.

c. Debonders Addition After Kemira Fennorez® 110

In this series of experiments, debonders were dosed after temporary wet strength resin Fennorez® 110 (7 #/T), a glyoxylated polyacrylamide type tWSR. The titratable charge of the zwitterion debonder cells remained the same slightly negative as the dose was increased, while the titratable charge of the Control debonder cell kept increasing and was positive at most testing points. The zeta potentials decreased as the zwitterion debonder doses increased as well. Here again, this implies that the debonder was being retained on the fibers, as shown in Table 5. In most cases, DBC1 debonded better than DBC2 and the Control debonder, CDB.

TABLE 5

Debonder added after Fennorez ® 110.

| Sample ID | Debonder | Dose (#/T) | Titratable Charge (ml/10 ml) | Zeta Potential (mV) | Basis Weight (gm/m²) | Dry Breaking Length (Km) |
|---|---|---|---|---|---|---|
| 1 | 0 | 0 | −0.07 | 32 | 52.66 | 2.34 |
| 2 | DBC2 | 2 | −0.06 | 22 | 53.28 | 2.05 |
| 3 | | 4 | −0.06 | 17 | 52.52 | 1.73 |
| 4 | | 6 | −0.06 | 13 | 53.34 | 1.56 |
| 5 | | 8 | −0.04 | 11 | 52.81 | 1.42 |
| 6 | DBC1 | 2 | −0.07 | 20 | 52.88 | 1.93 |
| 7 | | 4 | −0.05 | 14 | 53.36 | 1.77 |
| 8 | | 6 | −0.07 | 11 | 53.88 | 1.33 |
| 9 | | 8 | −0.07 | 9 | 54.19 | 1.42 |
| 10 | CDB | 2 | −0.01 | 34 | 53.20 | 1.71 |
| 11 | | 4 | 0.07 | 36 | 52.70 | 1.86 |
| 12 | | 6 | 0.10 | 40 | 53.08 | 1.42 |
| 13 | | 8 | 0.13 | 39 | 53.40 | 1.49 |

Figure 10:
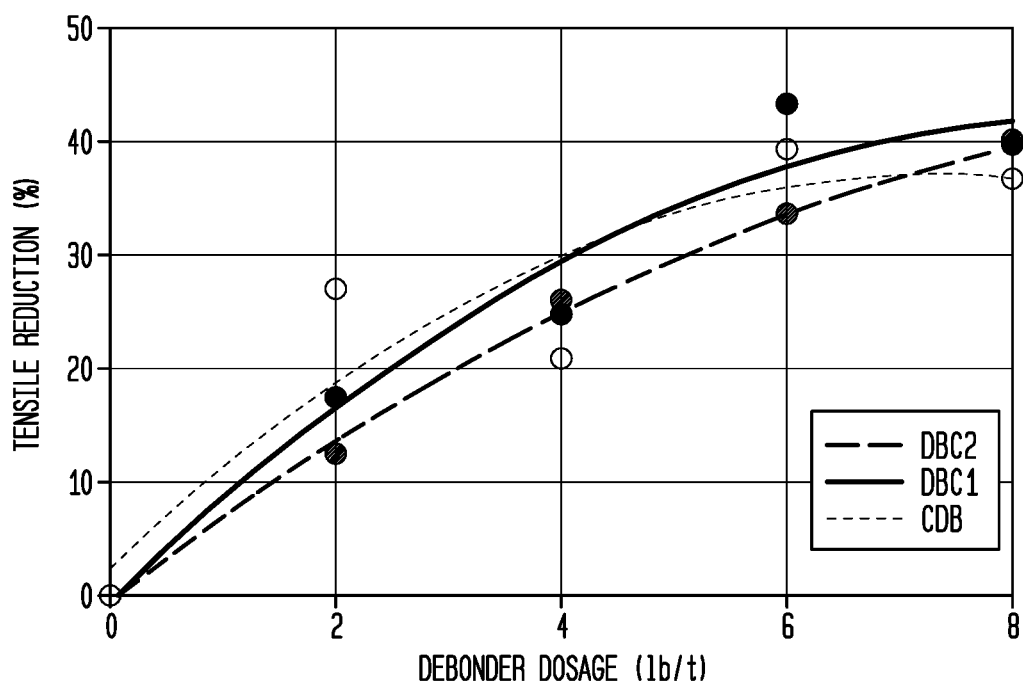
FIG. 10 is a plot of tensile reduction versus debonder dosage for handsheets, wherein the furnish was treated with cationic temporary wet strength resin prior to adding debonder.

Furnish = HW/SW dry lap (65/35)
All samples dosed with 7 #/T Kemira Fennorez ® 110 prior to debonder addition When dosed with tWSR, zwitterion debonder exhibited a similar tensile reduction as the cationic Control debonder, CDB as shown in FIG. 10.

It should be noted that: 1. Kemira Fennorez® 110 is a tWSR with relatively high cationic charge density; and 2. although debonder and tWSR were dosed together in trials, it is unusual in practice to dose debonder and tWSR at the same layer in connection with commercial manufacture. More commonly in commercial practice, when tWSR and debonder are used in an absorbent product a layered headbox is used and tWSR is added to that portion of the furnish making up the bottom layer of the product and debonder is added to that portion of the furnish making up the top layer of the product.

pWSR and debonder may be dosed together in the same layer for towel products when using a multilayer headbox.

Zwitterion debonder formulations tested did not debond handsheets when they were dosed by themselves due possibly to the stronger anionic properties of sulfonate type zwitterion debonders. However, when they were dosed with permanent wet strength resin (pWSR), DBC1 and DBC2 exhibited similar or better debond performance and better charge control compared to the Control CDB. Addition points of the debonders can greatly influence the tensile reduction of the handsheets; hence adding debonders prior to pWSR debonded better than adding after pWSR. When zwitterion debonders were dosed with temporary wet strength resin (tWSR), DBC1 outperformed DBC2 and CDB debonder in tensile reduction. DBC1 debonder exhibited best debond performance and charge control in both tissue and towel type handsheet production.

C. Ion Paired Surfactant Mixture Containing Debonders

Following generally the procedures noted above, additional debonder compositions were prepared and tested. In particular, ion paired surfactant mixtures of zwitterionic imidazolinium, Compound 1,

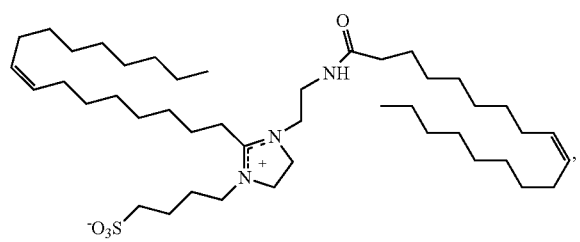

referred to as IM-SZ for present purposes, and cationic imidazolinium based on oleic acid, diethylene triamine and diethyl sulfate:

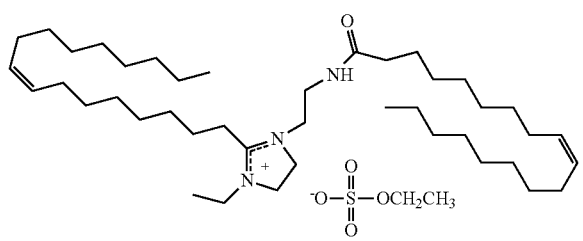

Cationic Imidazolinium (Im+)

were prepared and formulated in PEG-400 monooleate at a 15 wt. % level to prepare debonder compositions as noted in Table 6; also included was a control debonder based on Im+ and PEG monooleate only.

TABLE 6

Components and Charge Density of Different Debonder Formulations

| Debonder Composition | Mole ratio of Im+ (%) | Mole ratio of IM-SZ (%) | Total IM+ and IM-SZ in PEG-400 monooleate | Charge Density (meq/g) |
|---|---|---|---|---|
| CDB | 100 | 0 | 15 wt % | 0.32 |
| DBC1 | 0 | 100 | 15 wt % | −0.05 |
| DB-IP1 | 75 | 25 | 15 wt % | 0.21 |
| DB-IP2 | 50 | 50 | 15 wt % | 0.11 |
| DB-IP3 | 25 | 75 | 15 wt % | 0.06 |
| DB-IP4 | 85 | 15 | 15 wt % | 0.27 |
| DB-IP5 | 60 | 40 | 15 wt % | 0.20 |

Figure 11:
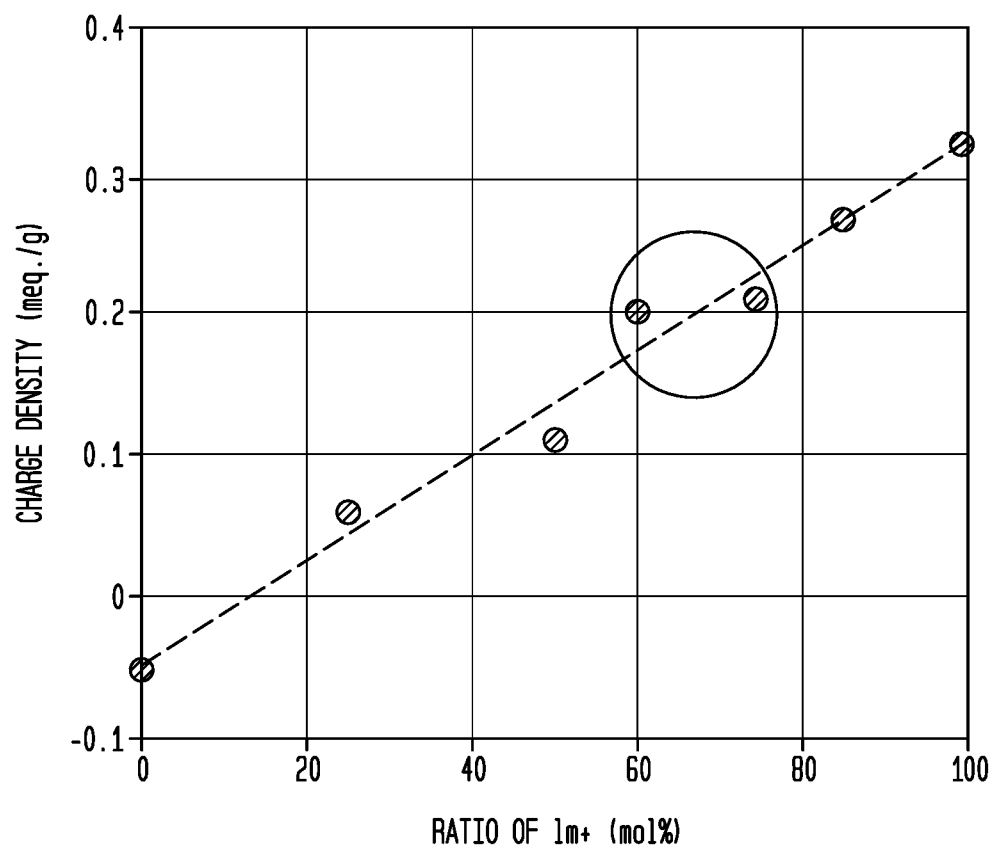
FIG. 11 is a plot of charge density of debonder formulations versus the ratio of cationic Im+ surfactant to zwitterionic in the mixture.

FIG. 11 is a plot of charge density of the formulations vs. the ratio of cationic Im+. The data shows a linear relationship between the charge density and the ratio of Im+ to zwitterionic surfactant.

For testing in Handsheets, a given 15 g (O.D. wt.) sample of an unrefined 30:70 mixture of softwood and hardwood furnish is diluted to 1500 ml using tap water, a given dosage of ion paired debonder formulation or CDB is added and stirred 2-3 min. The slurry is tested for titratable charge with either a 0.001 N solution of PolyDADMAC or PVSK using a Mutek instrument as detector. The salvageable components were recombined with the treated slurry and tested for zeta-potential with a Mutek SZP-10. The slurry is then diluted to 15 L, and formed into 1.0 gm British handsheets, pressed at 15 psi for 5 min, and dried on a rotating dryer drum at 250° F.

Results of a first series of tests on furnishes and Handsheets prepared with CDB, DB-IP1, DB-IP-2, DB-IP3 as well as sheet with no debonder appear in Table 7. Table 7 shows the charge, basis weight, caliper and breaking length data of the handsheet with CDB or ion-paired debonder formulations dosed. The titratable charge and zeta potential of ion-pairs debonder formulations are more negative compared to those of CDB at the same dosage. As the ratio of SZ-Im increased, the titratable charge and zeta potential decreased more.

TABLE 7

Handsheet Study Data of Different Debonder Formulations (I)

| Debonder | Dose (#/t) | Titratable Charge (ml/10 ml) | Zeta Potential (mV) | Basis Weight (g/m²) | Caliper (mils/5 sheets) | Breaking Length (km) |
|---|---|---|---|---|---|---|
|  | 0 | −0.13 | −67.6 | 53.51 | 27.22 | 1.80 |
| CDB | 4 | −0.09 | −47 | 53.17 | 27.15 | 1.23 |
| (100% | 6 | −0.07 | −38 | 34.01 | 27.82 | 1.09 |
| Im+) | 8 | −0.07 | −31.9 | 54.20 | 28.62 | 0.92 |
|  | 10 | −0.08 | −27.6 | 53.54 | 28.47 | 0.82 |
|  | 15 | −0.05 | −10.9 | 52.75 | 28.89 | 0.63 |
| DB-IP1 | 4 | −0.07 | −47.6 | 52.61 | 27.75 | 1.15 |
| (75% Im+ | 6 | −0.08 | −39.9 | 52.66 | 27.95 | 1.06 |
| 25% SZ- | 8 | −0.08 | −34.3 | 52.38 | 27.85 | 0.88 |
| Im] | 10 | −0.09 | −28.6 | 56.34 | 30.37 | 0.86 |
|  | 15 | −0.07 | −16.6 | 53.00 | 28.70 | 0.69 |
| DB-IP2 | 4 | −0.14 | −47.4 | 53.51 | 28.45 | 1.30 |
| (50% Im+ | 6 | −0.12 | −39.5 | 52.85 | 27.74 | 1.12 |
| 50% SZ- | 8 | −0.16 | −33.2 | 52.79 | 28.00 | 1.05 |
| Im) | 10 | −0.13 | −31.3 | 52.96 | 28.19 | 0.83 |
|  | 15 | −0.14 | −23.6 | 53.24 | 29.09 | 0.71 |
| DB-IP3 | 4 | −0.13 | −49.1 | 53.00 | 27.88 | 1.55 |
| (25% Im+ | 6 | −0.2 | −41.9 | 53.06 | 28.08 | 1.44 |
| 75% SZ- | 8 | −0.22 | −32.8 | 52.71 | 28.03 | 1.35 |
| Im] | 10 | −0.23 | −36.7 | 53.27 | 28.18 | 1.23 |
|  | 15 | −0.2 | −32.7 | 52.86 | 28.36 | 0.84 |

Figure 12:
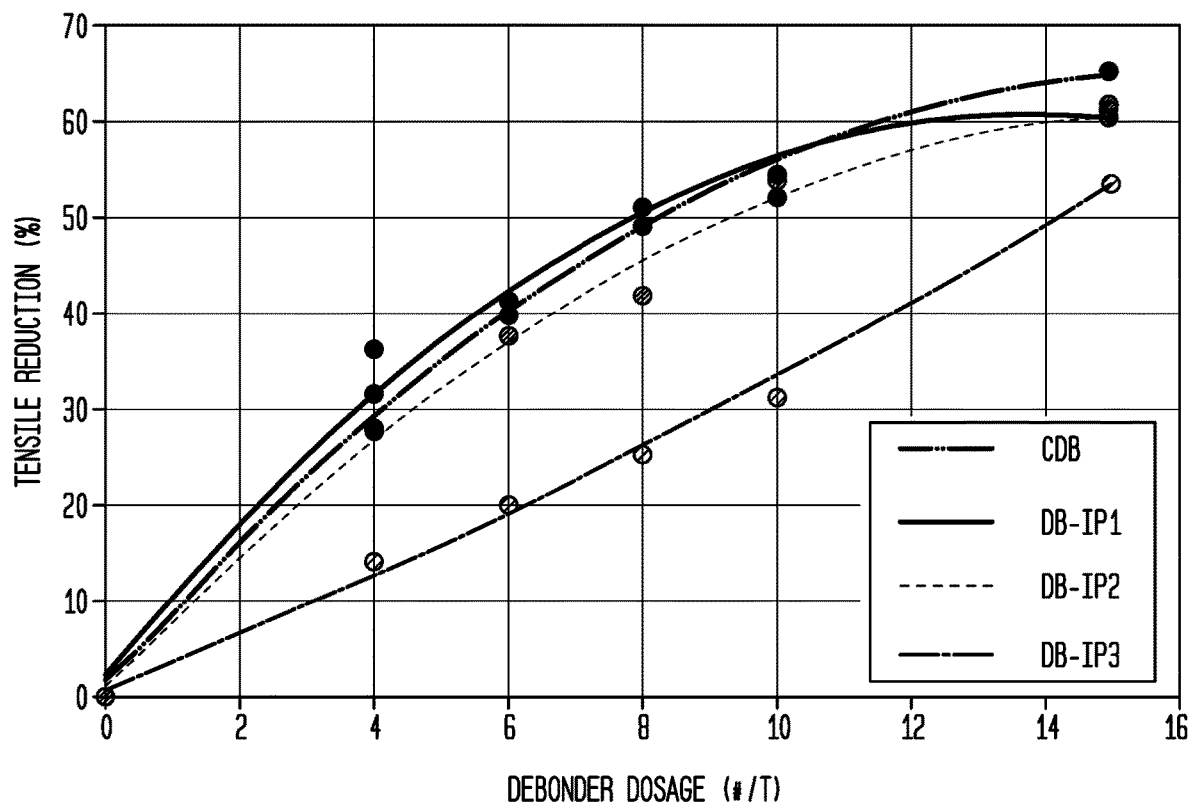
FIG. 12 is a plot of tensile reduction versus debonder dosage levels for tissue-type handsheets made with control debonder composition and ion paired debonder compositions DB-IP1, DB-IP2 and DB-IP3.

All three ion-pairs formulations DB-IP1, DB-IP-2, DB-IP3 debonded the handsheets. As shown in FIG. 12 the debonding performance improved as the cationic Im+ increased. DB-IP1 outperformed or performed similarly as CDB. Tensile reduction of the handsheets dosed with DB-IP2 was only slightly lower than that of handsheets dosed with CDB. DB-IP3 showed the best charge control, but did not debond as well as DB-IP1, DB-IP2 and CDB.

Following the first series of tests, a second series of tests on furnishes and handsheets prepared with CDB, DB-IP4, DB-IP-5 as well as sheet with no debonder were performed. Results appear in Table 8.

TABLE 8

Handsheet Study Data of Different Debonder Formulations (II)

| Debonder | Dose (#/t) | Titratable Charge (ml/10 ml) | Zeta Potential (mV) | Basis Weight (g/m²) | Caliper (mils/5 sheets) | Breaking Length (km) |
|---|---|---|---|---|---|---|
|  | 0 | −0.13 | −69.1 | 53.34 | 28.76 | 1.48 |
| CDB | 4 | −0.08 | −51.9 | 54.29 | 29.29 | 1.09 |
| (100% | 6 | −0.08 | −38.7 | 53.40 | 28.79 | 0.94 |
| Im+) | 8 | −0.07 | −34.6 | 53.86 | 29.90 | 0.74 |
|  | 10 | −0.07 | −26.2 | 53.67 | 30.15 | 0.67 |
|  | 15 | −0.08 | −13.1 | 53.46 | 31.25 | 0.53 |
| DB-IP4 | 4 | −0.08 | −51.1 | 54.51 | 30.11 | 1.04 |
| (85% Im+ | 6 | −0.07 | −39.4 | 54.42 | 30.10 | 0.90 |
| 15% SZ- | 8 | −0.08 | −32.5 | 53.93 | 29.97 | 0.74 |
| Im) | 10 | −0.07 | −26.5 | 54.09 | 31.08 | 0.75 |
|  | 15 | −0.07 | −12.2 | 54.34 | 31.66 | 0.56 |
| DB-IP5 | 4 | −0.09 | −50.8 | 54.73 | 30.36 | 1.03 |
| (60% Im+ | 6 | −0.07 | −43.3 | 54.34 | 29.57 | 0.93 |
| 40 SZ- | 8 | −0.09 | −37.4 | 54.29 | 30.36 | 0.75 |
| Im] | 10 | −0.1 | −31.4 | 55.06 | 31.42 | 0.72 |
|  | 15 | −0.11 | −19.1 | 54.96 | 31.89 | 0.50 |

Figure 13:
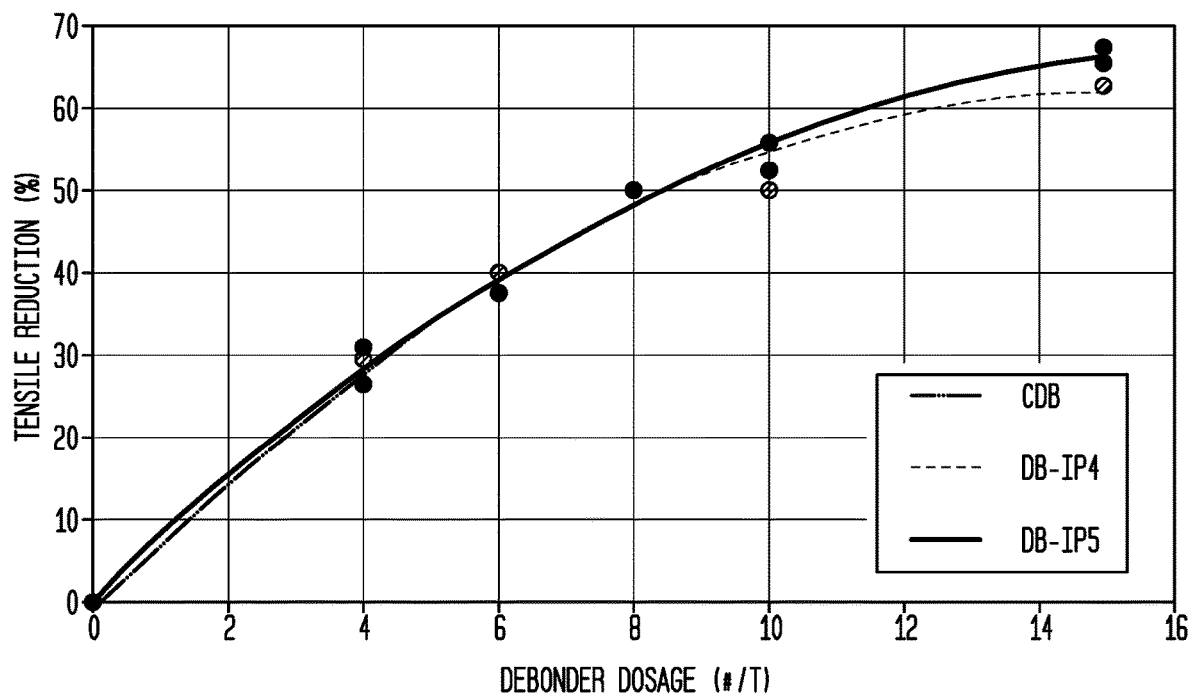
FIG. 13 is a plot of tensile reduction versus debonder dosage levels for tissue-type handsheets made with control debonder composition and ion paired debonder compositions DB-IP4 and DB-IP5.

As shown in FIG. 13, DB-IP4 and DB-IP5 performed similarly as CDB. Tensile reduction of DB-IP4 was only slightly lower than that of CDB at high dosage.

When the ratio of cationic Im+ was too high in an ion-pairs formulation (DB-IP4), it didn't show any advantages in charge control. On the other hand, when the ratio of cationic Im+ and zwitterionic SZ-Im was between 3:2 and 3:1, the ion-pairs formulations showed satisfactory charge control and enhanced debonding performance. Optimized debonding and charge control performance are likely related to the charge density of the debonder formulations. Formulations with charge density around 0.2 meq/g exhibited the optimized performance in practice. In FIG. 11, a circled area represents the best ratio range of Im+ and SZ-Im for the ion-paired debonder formulations.

Summary of Embodiments

There is thus provided in Embodiment No. 1 a method of making absorbent sheet comprising: (a) preparing an aqueous furnish of papermaking fibers; (b) incorporating a debonder composition into the aqueous furnish, said debonder composition comprising an imidazolinium surfactant-containing constituent selected from the group consisting of: (i) cationic imidazolinium surfactants with alkylalkenylhydroxy substitution; (ii) zwitterionic imidazolinium surfactants; and (iii) an ion paired surfactant mixture including a zwitterionic imidazolinium surfactant and a cationic surfactant and, in admixture with the imidazolinium surfactant-containing constituent, (iv) a nonionic surfactant; (c) incorporating a cationic wet strength resin into the aqueous furnish; and (d) forming the papermaking furnish into absorbent sheet.

Embodiment No. 2 is the method of making absorbent sheet according to Embodiment No. 1, wherein the debonder composition exhibits a charge density of from −0.1 to 0.3 meq/g.

Embodiment No. 3 is the method of making absorbent sheet according to Embodiment Nos. 1 or 2, wherein the debonder composition exhibits a charge density of 0.25 meq/g or less.

Embodiment No. 4 is the method of making absorbent sheet according to any of the foregoing Embodiments, wherein the debonder composition exhibits a charge density of from 0.175 to 0.225 meq/g or less.

Embodiment No. 5 is the method of making absorbent sheet according to any of the foregoing Embodiments, wherein the debonder composition comprises from 5 to 45 wt. % of imidazolinium surfactant-containing constituent and from 65 to 95 wt. % of nonionic surfactant.

Embodiment No. 6 is the method of making absorbent sheet according to any of the foregoing Embodiments, wherein the debonder composition comprises from 10 to 20 wt. % of imidazolinium surfactant-containing constituent and from 80 to 90 wt. % of nonionic surfactant.

Embodiment No. 7 is the method of making absorbent sheet according to any of the foregoing Embodiments wherein the debonder composition is incorporated into the aqueous furnish prior to incorporating the cationic wet strength resin into the aqueous furnish.

Embodiment No. 8 is the method of making absorbent sheet according to any of the foregoing Embodiments, wherein the cationic wet strength resin is incorporated into the aqueous furnish prior to incorporating the debonder composition into the aqueous furnish.

Embodiment No. 9 is the method according to any of the foregoing Embodiments, wherein the cationic wet strength resin is incorporated into the aqueous furnish at a level of from 2.5 to 30 lbs/ton of papermaking fiber.

Embodiment No. 10 is the method according to any of the foregoing Embodiments, wherein the cationic wet strength resin is incorporated into the aqueous furnish at a level of from 5 to 25 lbs/ton of papermaking fiber.

Embodiment No. 11 is the method according to any of the foregoing Embodiments, wherein the cationic wet strength resin comprises a polyamidoamine epichlorohydrin permanent wet strength resin.

Embodiment No. 12 is the method according to any of the foregoing Embodiments, wherein the cationic wet strength resin comprises a glyoxylated polyacrylamide temporary wet strength resin.

Embodiment No. 13 is the method according to any of the foregoing Embodiments, wherein the debonder composition is incorporated into the aqueous furnish at a level of from 1 to 30 lbs debonder composition per ton of papermaking fiber.

Embodiment No. 14 is the method according to any of the foregoing Embodiments, wherein the debonder composition is incorporated into the aqueous furnish at a level of from 2 to 25 lbs debonder composition per ton of papermaking fiber.

Embodiment No. 15 is the method according to any of the foregoing Embodiments, wherein the debonder composition is incorporated into the aqueous furnish at a level of from 2 to 16 lbs debonder composition per ton of papermaking fiber.

Embodiment No. 16 is the method according to any of the foregoing Embodiments, wherein the debonder composition comprises a nonionic surfactant selected from alkoxylated fatty acids and alkoxylated fatty alcohols.

Embodiment No. 17 is the method according to any of the foregoing Embodiments, wherein the debonder composition comprises the reaction product of a fatty acid or fatty alcohol with ethylene oxide.

Embodiment No. 18 is the method according to any of the foregoing Embodiments, wherein the debonder composition comprises a mixture of mono- and diesters of one or more fatty acids.

Embodiment No. 19 is the method according to Embodiment No. 18, wherein the mixture of mono- and diesters of the fatty acid(s) are a mixture of PEG monoesters and PEG diesters having a PEG chain molecular weight in the range of 200 to 800.

Embodiment No. 20 is the method according to any of the foregoing Embodiments, wherein the imidazolinium surfactant-containing constituent is selected from the group consisting of: cationic imidazolinium surfactants bearing both a hydroxy substituted alkylalkenyl substituent having from 11 to 21 carbon atoms and an amidoalkenylalkyl moiety bearing a pendant hydroxyl group having from 12 to 22 carbon atoms and zwitterionic imidazolinium surfactants having a substituent with from 8 to 30 carbon atoms.

Embodiment No. 21 is a cationic imidazolinium surfactant of the formula:

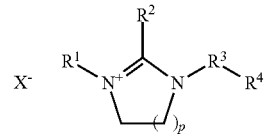

wherein:
R$^1$ is H, methyl, ethyl, or propyl;
R$^2$ is a hydroxy substituted alkylalkenyl moiety having from 11 to 21 carbon atoms;
R$^3$ is an ethylene or propylene bridging group;
R$^4$ is an amidoalkenylalkyl moiety bearing a pendant hydroxyl group having from 12 to 22 carbon atoms;
p is 1 or 2; and
X is selected from halides, sulfates, carboxylates and phosphates.

Embodiment No. 22 is the cationic imidazolinium surfactant according to Embodiment No. 21, wherein X is selected from Cl, Br, CH$_3$OSO$_3$, C$_2$H$_5$OSO$_3$, NO$_3$, HCOO and CH$_3$COO.

Embodiment No. 23 is the cationic imidazolinium surfactant according to Embodiment Nos. 21 or 22, wherein p is 1.

Embodiment No. 24 is the cationic imidazolinium surfactant according to Embodiment Nos. 21, 22 or 23, wherein R$^2$ is a hydroxy substituted alkenyl moiety having from 14 to 19 carbon atoms.

Embodiment No. 25 is the cationic imidazolinium surfactant according to Embodiment No. 24, wherein R$^2$ is a hydroxy substituted alkenyl moiety having from 15 to 18 carbon atoms.

Embodiment No. 26 is the cationic imidazolinium surfactant according to Embodiment No. 25, wherein R$^2$ is:

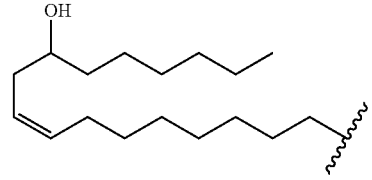 [SMILES: *CCCCCCC/C=C\CC(O)CCCCCC]

Embodiment No. 27 is the cationic imidazolinium surfactant according to any of Embodiment Nos. 21-26, wherein R$^3$ is —C$_2$H$_4$—.

Embodiment No. 28 is the cationic imidazolinium surfactant according to any of Embodiment Nos. 21-27, wherein R$^4$ is an amidoalkenylalkyl moiety bearing a pendant hydroxyl group having from 14 to 22 carbon atoms.

Embodiment No. 29 is the cationic imidazolinium surfactant according to Embodiment No. 28, wherein $R^4$ is an amidoalkenylalkyl moiety bearing a pendant hydroxyl group having from 16 to 20 carbon atoms.

Embodiment No. 30 is the cationic imidazolinium surfactant according to Embodiment No. 29, wherein $R^4$ is:

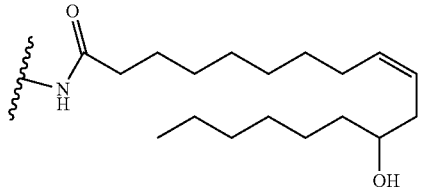 [SMILES: *NC(=O)CCCCCCC/C=C\CC(O)CCCCCC]

Embodiment No. 31 is a debonder composition for absorbent paper manufacture comprising a cationic imidazolinium surfactant of any of Embodiment Nos. 21-30 in admixture with a nonionic surfactant.

Embodiment No. 32 is the debonder composition according to Embodiment No. 31, wherein the debonder composition comprises from 5 to 45 wt. % of cationic imidazolinium surfactant and from 65 to 95 wt. % of nonionic surfactant.

Embodiment No. 33 is the debonder composition according to Embodiment No. 32, wherein the debonder composition comprises from 10 to 20 wt. % of cationic imidazolinium surfactant and from 80 to 90 wt. % of nonionic surfactant.

Embodiment No. 34 is the debonder composition according to any of Embodiment Nos. 31-33, wherein the debonder composition comprises a nonionic surfactant selected from alkoxylated fatty acids and alkoxylated fatty alcohols.

Embodiment No. 35 is the debonder composition according to Embodiment No. 34, wherein the debonder composition comprises the reaction product of a fatty acid or fatty alcohol with ethylene oxide.

Embodiment No. 36 is the debonder composition according to Embodiment Nos. 34 or 35, wherein the debonder composition comprises a mixture of mono- and diesters of one or more fatty acids.

Embodiment No. 37 is the debonder composition according to Embodiment No. 36, wherein the mixture of mono- and diesters of the fatty acid(s) are a mixture of PEG monoesters and PEG diesters having a PEG chain molecular weight in the range of 200 to 800.

Embodiment No. 38 is the debonder composition according to any of Embodiment Nos. 31-37, wherein the debonder composition exhibits a charge density of 0.25 meq/g or less.

Embodiment No. 39 is the debonder composition according Embodiment No. 38, wherein the debonder composition exhibits a charge density of 0.20 meq/g or less.

Embodiment No. 40 is the debonder composition according to any of Embodiment Nos. 31-37 or Embodiment No. 39, wherein the debonder composition exhibits a charge density of from 0.10 meq/g to 0.20 meq/g.

Embodiment No. 41 is an ion paired surfactant mixture useful for debonder and softener compositions utilized in absorbent paper manufacture, said mixture comprising a zwitterionic imidazolinium surfactant and a cationic surfactant selected from cationic imidazolinium surfactants and quaternary ammonium surfactants, said zwitterionic imidazolinium surfactant having the structural formula I:

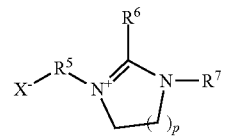

wherein:

$R^5$ is a straight or branched hydrocarbon spacer moiety having from 2-18 carbon atoms wherein said $R^5$ may be unsubstituted or optionally substituted with one or more groups which can be the same or different and are independently selected from the group consisting of halogen, cyano, alkyl, cycloalkyl, —OH, O($C_1$-$C_6$) alkyl, —C(=O)($C_1$-$C_6$) alkyl, —$CO_2$H, —C(=O)O($C_1$-$C_6$) alkyl, N[($C_1$-$C_6$) alkyl]$_2$, and —NH[($C_1$-$C_6$) alkyl] and/or may have interposed within said hydrocarbon spacer moiety one or more groups which may be the same or different and are independently selected from the group consisting of —NH—C(O)—, —C(O)—NH—, —O—, —$SO_2$— and —C(=O)—;

$R^6$ is a straight or branched saturated or unsaturated hydrocarbon moiety having from 3 to 30 carbon atoms wherein said $R^6$:

(i) may be unsubstituted or optionally substituted with one or more groups which can be the same or different and are independently selected from the group consisting of halogen, cyano, alkyl, cycloalkyl, —OH, O($C_1$-$C_6$) alkyl, —$CO_2$H, —C(=O)($C_1$-$C_6$) alkyl, —C(=O)O ($C_1$-$C_6$) alkyl, —N[($C_1$-$C_6$) alkyl]$_2$, —NH—C(O)($C_1$-$C_6$) alkyl, —C(O)$NH_2$, —C(O)—NH($C_1$-$C_6$) alkyl, and —NH($C_1$-$C_6$) alkyl, and/or (ii) may have interposed within said hydrocarbon moiety one or more groups which may be the same or different and are independently selected from the group consisting of —NH—C(O)—, —C(O)—NH—, —O—, —$SO_2$— and —C(=O)—;

$R^7$ is a straight or branched saturated or unsaturated hydrocarbon moiety having from 3 to 30 carbon atoms wherein said $R^7$:

(i) may be unsubstituted or optionally substituted with one or more groups which can be the same or different and are independently selected from the group consisting of halogen, cyano, alkyl, cycloalkyl, —OH, O($C_1$-$C_6$) alkyl, —$CO_2$H, —C(=O)($C_1$-$C_6$) alkyl, —C(=O)O ($C_1$-$C_6$) alkyl, —N[($C_1$-$C_6$) alkyl]$_2$, —NH—C(O)($C_1$-$C_6$) alkyl, —C(O)$NH_2$, —C(O)—NH($C_1$-$C_6$) alkyl, and —NH($C_1$-$C_6$) alkyl, and/or (ii) may have interposed within said hydrocarbon moiety one or more groups which may be the same or different and are independently selected from the group consisting of —NH—C(O)—, —C(O)—NH—, —O—, —$SO_2$— and —C(=O)—;

wherein at least one of $R^6$ or $R^7$ or has from 8 to 30 carbon atoms;

X is selected from the group consisting of $SO_3$, $CO_2$, $PO_2$ and $HPO_2$; and p is 1 or 2.

Embodiment No. 42 is the ion paired surfactant mixture useful for debonder and softener compositions utilized in absorbent paper manufacture according to Embodiment No. 41, wherein $R^6$ and $R^7$ have from 8 to 30 carbon atoms Embodiment No. 43 is the ion paired surfactant mixture useful for debonder and softener compositions utilized in absorbent paper manufacture according to Embodiment Nos. 41 or 42, wherein:

R⁵ is a hydrocarbyl spacer group having a chain length of from 2-6 carbon atoms;
R⁶ is a hydrocarbyl group having from 8 to 22 carbon atoms; and
R⁷ is an alkenylamidoalkyl moiety having from 8 to 22 carbon atoms.

Embodiment No. 44 is the ion paired surfactant mixture useful for debonder and softener compositions utilized in absorbent paper manufacture according to Embodiment No. 43 wherein R⁵ is an alkylene group of the formula (—CH₂-)ₙ wherein n is an integer from 2 to 6.

Embodiment No. 45 is the ion paired surfactant mixture useful for debonder and softener compositions utilized in absorbent paper manufacture according to any of Embodiment Nos. 41-44, wherein R⁶ is an alkenyl substituent with from 10 to 20 carbon atoms.

Embodiment No. 46 is the ion paired surfactant mixture useful for debonder and softener compositions utilized in absorbent paper manufacture according to any of Embodiment Nos. 41-45, wherein R⁷ is an alkenylamidoalkyl moiety of the formula:

wherein R8 is an alkenyl group and m is an integer from 2 to 10.

Embodiment No. 47 is the ion paired surfactant mixture useful for debonder and softener compositions utilized in absorbent paper manufacture according to Embodiment No. 46, wherein R8 is an alkenyl substituent having from 10-20 carbon atoms.

Embodiment No. 48 is the ion paired surfactant mixture useful for debonder and softener compositions utilized in absorbent paper manufacture according to any of Embodiment Nos. 41-47, comprising a cationic imidazolinium surfactant, wherein the cationic surfactant has the structural formula:

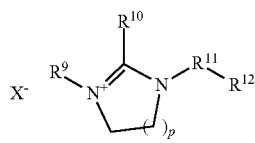

wherein:
R⁹ is H, methyl, ethyl, or propyl;
R¹⁰ is an alkylalkenyl moiety having from 11 to 21 carbon atoms;
R¹¹ is an ethylene or propylene bridging group;
R¹¹ is an amidoalkenylalkyl moiety having from 12 to 22 carbon atoms;
p is 1 or 2; and
X is selected from halides, sulfates, carboxylates and phosphates.

Embodiment No. 49 is the ion paired surfactant mixture useful for debonder and softener compositions utilized in absorbent paper manufacture according to Embodiment No. 48, wherein X is selected from Cl, Br, CH₃OSO₃, C₂H₅OSO₃, NO₃, HCOO and CH₃COO.

Embodiment No. 50 is the ion paired surfactant mixture useful for debonder and softener compositions utilized in absorbent paper manufacture according to Embodiment Nos. 48 or 49, wherein p is 1.

Embodiment No. 51 is the ion paired surfactant mixture useful for debonder and softener compositions utilized in absorbent paper manufacture according to any of Embodiment Nos. 48-50, wherein R¹⁰ is a hydroxy substituted alkenyl moiety.

Embodiment No. 52 is the ion paired surfactant mixture useful for debonder and softener compositions utilized in absorbent paper manufacture according to Embodiment No. 51, wherein R¹⁰ is:

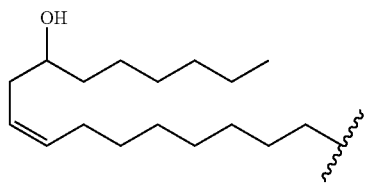 [SMILES: *CCCCCCC/C=C\CC(O)CCCCCC]

Embodiment No. 53 is the ion paired surfactant mixture useful for debonder and softener compositions utilized in absorbent paper manufacture according to any of Embodiment Nos. 48-52, wherein R¹¹ is —C₂H₄—.

Embodiment No. 54 is the ion paired surfactant mixture useful for debonder and softener compositions utilized in absorbent paper manufacture according to any of Embodiment Nos. 48-53, wherein R¹² is an amidoalkenylalkyl moiety bearing a pendant hydroxyl group.

Embodiment No. 55 is the ion paired surfactant mixture useful for debonder and softener compositions utilized in absorbent paper manufacture according to Embodiment No. 54, wherein R¹² is:

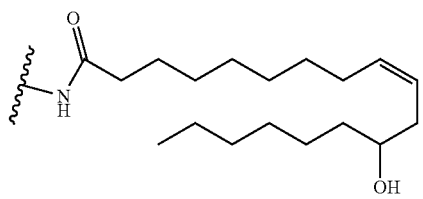 [SMILES: *NC(=O)CCCCCCC/C=C\CC(O)CCCCCC]

Embodiment No. 56 is the ion paired surfactant mixture useful for debonder and softener compositions utilized in absorbent paper manufacture according to any of Embodiment Nos. 41-47, comprising a quaternary ammonium surfactant.

Embodiment No. 57 is the ion paired surfactant mixture useful for debonder and softener compositions utilized in absorbent paper manufacture according to Embodiment No. 56, wherein the quaternary ammonium surfactant is selected from the group consisting of:

a dialkyldimethylammonium compound of the formula:

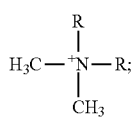

and
a bis-dialkylamidoammonium compound of the formula:

$$\text{RCONHCH}_2\text{CH}_2\underset{\underset{\text{CH}_3}{|}}{\overset{\overset{\text{CH}_2-\text{CH}_2\text{OH}}{|}}{-^+\text{N}-}}\text{CH}_2\text{CH}_2\text{NHCOR}$$

wherein each R may be the same or different and each R indicates a hydrocarbon chain, saturated or unsaturated, having a chain length of from about twelve to about twenty-two carbon atoms; and wherein said compounds are supplied to the surfactant mixture with a suitable anion.

Embodiment No. 58 is the ion paired surfactant mixture useful for debonder and softener compositions utilized in absorbent paper manufacture according to Embodiment No. 57, wherein the anion is selected from $Cl^-$, $Br^-$, $CH_3OSO_3^-$, $C_2H_5OSO_3^-$, $NO_3^-$, $HCOO^-$ and $CH_3COO^-$.

Embodiment No. 59 is the ion paired surfactant mixture according to any of Embodiment Nos. 41-58, wherein the molar ratio of cationic surfactant to zwitterionic surfactant is from 90:10 to 10:90.

Embodiment No. 60 is the ion paired surfactant mixture according to Embodiment No. 59, wherein the molar ratio of cationic surfactant to zwitterionic surfactant is from 85:15 to 15:85.

Embodiment No. 61 is the ion paired surfactant mixture according to Embodiment No. 60, wherein the molar ratio of cationic surfactant to zwitterionic surfactant is from 75:25 to 25:75.

Embodiment No. 62 is the ion paired surfactant mixture according to Embodiment No. 61, wherein the molar ratio of cationic surfactant to zwitterionic surfactant is from 55:45 to 80:20.

Embodiment No. 63 is the ion paired surfactant mixture according to Embodiment No. 62, wherein the molar ratio of cationic surfactant to zwitterionic surfactant is from 60:40 to 75:25.

Embodiment No. 64 is a debonder composition for absorbent paper manufacture comprising the ion paired surfactant mixture of any of Embodiment Nos. 41-63 in admixture with a nonionic surfactant.

Embodiment No. 65 is the debonder composition according to Embodiment No. 64, wherein the debonder composition comprises from 5 to 45 wt. % of the ion paired surfactant mixture and from 65 to 95 wt. percent of nonionic surfactant.

Embodiment No. 66 is the debonder composition according to Embodiment No. 65, wherein the debonder composition comprises from 10 to 20 wt. % of the ion paired surfactant mixture and from 80 to 90 wt. % of nonionic surfactant.

Embodiment No. 67 is the debonder composition according to Embodiment Nos. 64-66, wherein the debonder composition comprises a nonionic surfactant selected from alkoxylated fatty acids and alkoxylated fatty alcohols.

Embodiment No. 68 is the debonder composition according to Embodiment No. 67, wherein the debonder composition comprises a mixture of mono- and diesters of one or more fatty acids.

Embodiment No. 69 is the debonder composition according to Embodiment No. 68, wherein the mixture of mono- and diesters of the fatty acid(s) are a mixture of PEG monoesters and PEG diesters having a PEG chain molecular weight in the range of 200 to 800 Daltons.

Embodiment No. 70 is the debonder composition according to any of Embodiment Nos. 64-69, wherein the debonder composition exhibits a charge density of from −0.1 to 0.3 meq/g.

Embodiment No. 71 is the debonder composition according to Embodiment No. 70, wherein the debonder composition exhibits a charge density of from 0.025 meq/g to 0.25 meq/g.

Embodiment No. 72 is the debonder composition according to Embodiment No. 71, wherein the debonder composition exhibits a charge density of from 0.15 to 0.25 meq/g.

Embodiment No. 73 is the debonder composition according to Embodiment No. 72 wherein the debonder composition exhibits a charge density of from 0.175 to 0.225 meq/g.

Embodiment No. 74 is a zwitterionic surfactant compound useful for debonder and softener compositions utilized in absorbent paper manufacture, said compound having the formula I:

$$(I)$$

$$X^-\underset{}{\overset{R^{13}}{\diagdown}}\underset{\underset{)_p}{}}{\overset{\overset{R^{14}}{|}}{N^+}}\diagdown N-R^{15}$$

wherein:
R$^{13}$ is a straight or branched hydrocarbon spacer moiety having from 2-18 carbon atoms wherein said R$^1$ may be unsubstituted or optionally substituted with one or more groups which can be the same or different and are independently selected from the group consisting of halogen, cyano, alkyl, cycloalkyl, —OH, O($C_1$-$C_6$) alkyl, —C(=O)($C_1$-$C_6$) alkyl, —$CO_2$H, —C(=O)O($C_1$-$C_6$) alkyl, N[($C_1$-$C_6$) alkyl]$_2$, and —NH[($C_1$-$C_6$) alkyl] and/or may have interposed within said hydrocarbon spacer moiety one or more groups which may be the same or different and are independently selected from the group consisting of —NH—C(O)—, —C(O)—NH—, —O—, —$SO_2$— and —C(=O)—;

R$^{14}$ is a straight or branched saturated or unsaturated hydrocarbon moiety having from 3 to 30 carbon atoms wherein said R$^{14}$:
(i) may be unsubstituted or optionally substituted with one or more groups which can be the same or different and are independently selected from the group consisting of halogen, cyano, alkyl, cycloalkyl, —OH, O($C_1$-$C_6$) alkyl, —$CO_2$H, —C(=O)($C_1$-$C_6$) alkyl, —C(=O)O($C_1$-$C_6$) alkyl, —N[($C_1$-$C_6$) alkyl]$_2$, —NH—C(O)($C_1$-$C_6$) alkyl, —C(O)NH$_2$, —C(O)—NH($C_1$-$C_6$) alkyl, and —NH ($C_1$-$C_6$) alkyl, and/or
(ii) may have interposed within said hydrocarbon moiety one or more groups which may be the same or different and are independently selected from the group consisting of —NH—C(O)—, —C(O)—NH—, —O—, —$SO_2$— and —C(=O)—;

R$^{15}$ is a straight or branched saturated or unsaturated hydrocarbon moiety having from 3 to 30 carbon atoms wherein said R$^{15}$:
(i) may be unsubstituted or optionally substituted with one or more groups which can be the same or different and are independently selected from the group consisting of halogen, cyano, alkyl, cycloalkyl, —OH, O(C₁-C₆) alkyl, —CO₂H, —C(=O)(C₁-C₆) alkyl, —C(=O)O(C₁-C₆) alkyl, —N[(C₁-C₆) alkyl]₂, —NH—C(O)(C₁-C₆) alkyl, —C(O)NH₂, —C(O)—NH(C₁-C₆) alkyl, and —NH (C₁-C₆) alkyl, and/or (ii) may have interposed within said hydrocarbon moiety one or more groups which may be the same or different and are independently selected from the group consisting of —NH—C(O)—, —C(O)—NH—, —O—, —SO₂— and —C(=O)—;

wherein at least one of R¹⁴ or R¹⁵ has from 8 to 30 carbon atoms;

X is selected from the group consisting of SO₃, CO₂, PO₃ and HPO₂; and p is 1 or 2.

Embodiment No. 75 is the zwitterionic surfactant compound of Embodiment No. 74, wherein R¹⁴ and R¹⁵ have from 8 to 30 carbon atoms.

Embodiment No. 76 is the zwitterionic surfactant compound of Embodiment Nos. 74 or 75, wherein X is SO₃.

Embodiment No. 77 is the zwitterionic surfactant compound of Embodiment Nos. 74, 75 or 76, wherein said compound of formula I is an imidazolinium compound of formula II:

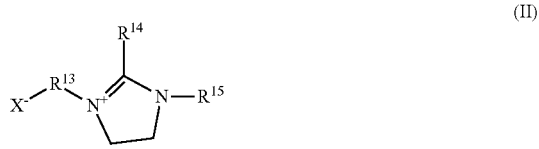

(II)

Embodiment No. 78 is the zwitterionic surfactant compound of Embodiment No. 77 wherein in said compound of formula II, X is SO₃.

Embodiment No. 79 is the zwitterionic surfactant compound of Embodiment Nos. 77 or 78, wherein:

R¹³ is a hydrocarbyl spacer group having a chain length of from 2-6 carbon atoms;

R¹⁴ is a hydrocarbyl group having from 8 to 22 carbon atoms; and

R¹⁵ is an alkenylamidoalkyl moiety having from 8 to 22 carbon atoms.

Embodiment No. 80 is the zwitterionic surfactant compound according to Embodiment No. 79, wherein R¹³ is an alkylene group of the formula (—CH₂-)ₙ wherein n is an integer from 2 to 6.

Embodiment No. 81 is the zwitterionic surfactant compound according to Embodiment No. 80, wherein n is 3 or 4.

Embodiment No. 82 is the zwitterionic surfactant compound according to any of Embodiment Nos. 77 through 81, wherein R¹⁴ is an alkenyl substituent.

Embodiment No. 83 is the zwitterionic surfactant compound according to Embodiment No. 82, wherein R¹⁴ is an alkenyl substituent with from 10 to 20 carbon atoms.

Embodiment No. 84 is the zwitterionic surfactant compound according to any of Embodiment Nos. 77 through 83, wherein R¹⁵ is an alkenylamidoalkyl moiety of the formula:

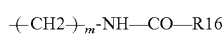

wherein R16 is an alkyl or alkenyl group and m is an integer from 2 to 10.

Embodiment No. 85 is the zwitterionic surfactant compound according to Embodiment No. 84, wherein m is an integer of from 2 to 6.

Embodiment No. 86 is the zwitterionic surfactant compound according to Embodiment Nos. 84 or 85, wherein R16 is an alkenyl substituent having from 10-20 carbon atoms.

Embodiment No. 87 is the zwitterionic surfactant compound according to Embodiment No. 86, wherein R16 is an alkenyl substituent having from 12-18 carbon atoms.

Embodiment No. 88 is a debonder composition for absorbent paper manufacture comprising the zwitterionic surfactant compound of any of Embodiment Nos. 74-87 in admixture with a nonionic surfactant.

Embodiment No. 89 is the debonder composition according to Embodiment No. 88, wherein the debonder composition comprises from 5 to 45 wt. % of the zwitterionic surfactant compound and from 65 to 95 wt. percent of nonionic surfactant.

Embodiment No. 90 is the debonder composition according to Embodiment No. 89, wherein the debonder composition comprises from 10 to 20 wt. % of the zwitterionic surfactant compound and from 80 to 90 wt. % of nonionic surfactant.

Embodiment No. 91 is the debonder composition according to Embodiment Nos. 88-90, wherein the debonder composition comprises a nonionic surfactant selected from alkoxylated fatty acids and alkoxylated fatty alcohols.

Embodiment No. 92 is the debonder composition according to Embodiment No. 91, wherein the debonder composition comprises a mixture of mono- and diesters of one or more fatty acids.

Embodiment No. 93 is the debonder composition according to Embodiment No. 92, wherein the mixture of mono- and diesters of the fatty acid(s) are a mixture of PEG monoesters and PEG diesters having a PEG chain molecular weight in the range of 200 to 800 Daltons.

Embodiment No. 94 is the debonder composition according to any of Embodiment Nos. 88-93, wherein the debonder composition exhibits a charge density of from −0.1 to 0.3 meq/g.

Embodiment No. 95 is the debonder composition according to Embodiment No. 94, wherein the debonder composition exhibits a charge density of 0.25 meq/g or less.

Embodiment No. 96 is the debonder composition according to Embodiment No. 95, wherein the debonder composition exhibits a charge density of 0.20 meq/g or less.

Embodiment No. 97 is the debonder composition according to Embodiment No. 96 wherein the debonder composition exhibits a charge density of from 0.025 meq/g to 0.15 meq/g.

Embodiment No. 98 is a method of making absorbent sheet according to any of Embodiment Nos. 1-19, utilizing a debonder composition of any of Embodiment Nos. 31-40.

Embodiment No. 99 is a method of making absorbent sheet according to any of Embodiment Nos. 1-19, utilizing a debonder composition of any of Embodiment Nos. 64-73.

Embodiment No. 100 is a method of making absorbent sheet according to any of Embodiment Nos. 1-19, utilizing a debonder composition of any of Embodiment Nos. 88-97.

While the invention has been described in detail, modifications within the spirit and scope of the invention will be readily apparent to those of skill in the art. Such modifications are also to be considered as part of the present invention. In view of the foregoing discussion, relevant knowledge in the art and references discussed above in connection with the foregoing description including the Background of the Invention, the disclosures of which are all incorporated herein by reference, further description is deemed unnecessary. In addition, it should be understood

What is claimed is:

1. A cationic imidazolinium surfactant of the formula:

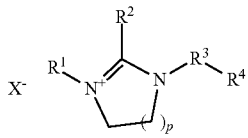

wherein:
$R^1$ is H, methyl, ethyl, or propyl;
$R^2$ is a hydroxy substituted alkylalkenyl moiety having from 11 to 21 carbon atoms;
$R^3$ is an ethylene or propylene bridging group;
$R^4$ is an amidoalkenylalkyl moiety bearing a pendant hydroxyl group having from 12 to 22 carbon atoms;
p is 1 or 2; and
X is selected from halides, sulfates, carboxylates and phosphates.

2. The cationic imidazolinium surfactant according to claim 1, wherein $R^2$ is:

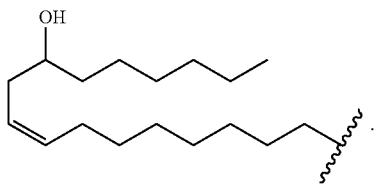 [SMILES: *CCCCCCC/C=C\CC(O)CCCCCC]

3. The cationic imidazolinium surfactant according to claim 1, wherein $R^4$ is:

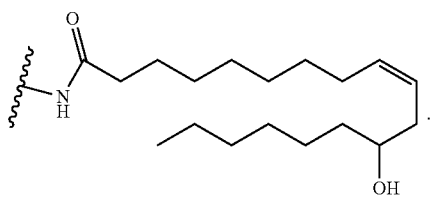 [SMILES: *NC(=O)CCCCCCC/C=C\CC(O)CCCCCC]

4. A debonder composition for absorbent paper manufacture comprising a cationic imidazolinium surfactant of claim 1 in admixture with a nonionic surfactant.

5. The debonder composition according to claim 4, wherein the debonder composition comprises from 5 to 45 wt. % of cationic imidazolinium surfactant and from 65 to 95 wt. % of nonionic surfactant.

6. The debonder composition according to claim 4, wherein the debonder composition exhibits a charge density of 0.20 meq/g or less.

7. The debonder composition according to claim 6, wherein the debonder composition exhibits a charge density of from 0.10 meq/g to 0.20 meq/g.

8. A method of making absorbent sheet comprising:
(a) preparing an aqueous furnish of papermaking fibers;
(b) incorporating a debonder composition into the aqueous furnish, said debonder composition comprising:
(i) an imidazolinium surfactant according to claim 1, and,
(ii) in admixture with the imidazolinium surfactant, a nonionic surfactant;
(c) incorporating a cationic wet strength resin into the aqueous furnish; and
(d) forming the papermaking furnish into absorbent sheet.

9. The method of making absorbent sheet according to claim 8, wherein the debonder composition exhibits a charge density of from −0.1 to 0.3 meq/g.

10. The method of making absorbent sheet according to claim 9, wherein the debonder composition exhibits a charge density of 0.25 meq/g or less.

11. The method of making absorbent sheet according to claim 10, wherein the debonder composition exhibits a charge density of from 0.175 to 0.225 meq/g.

12. The method according to claim 8, wherein the cationic wet strength resin is incorporated into the aqueous furnish at a level of from 2.5 to 30 lbs/ton of papermaking fiber.

13. The method according to claim 8, wherein the cationic wet strength resin is incorporated into the aqueous furnish at a level of from 5 to 25 lbs/ton of papermaking fiber.

14. The method according to claim 8, wherein the cationic wet strength resin comprises a polyamidoamine epichlorohydrin permanent wet strength resin.

15. The method according to claim 8, wherein the cationic wet strength resin comprises a glyoxylated polyacrylamide temporary wet strength resin.

16. The method according to claim 8, wherein the debonder composition is incorporated into the aqueous furnish at a level of from 1 to 30 lbs debonder composition per ton of papermaking fiber.

17. The method according to claim 8, wherein the debonder composition is incorporated into the aqueous furnish at a level of from 2 to 25 lbs debonder composition per ton of papermaking fiber.

18. The method according to claim 8, wherein the debonder composition is incorporated into the aqueous furnish at a level of from 2 to 16 lbs debonder composition per ton of papermaking fiber.

* * * * *